US009568462B2

(12) United States Patent
Reed

(10) Patent No.: US 9,568,462 B2
(45) Date of Patent: Feb. 14, 2017

(54) METHODS AND INSTRUMENTATION FOR DURING-SYNTHESIS MONITORING OF POLYMER FUNCTIONAL EVOLUTION

(71) Applicant: The Administrators of the Tulane Educational Fund, New Orleans, LA (US)

(72) Inventor: Wayne F. Reed, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 14/851,281

(22) Filed: Sep. 11, 2015

(65) Prior Publication Data
US 2016/0033470 A1 Feb. 4, 2016

Related U.S. Application Data

(63) Continuation of application No. 12/479,052, filed on Jun. 5, 2009.
(Continued)

(51) Int. Cl.
*C08F 2/00* (2006.01)
*A61L 2/28* (2006.01)
(Continued)

(52) U.S. Cl.
CPC ......... *G01N 33/442* (2013.01); *B01J 19/0033* (2013.01); *C08F 2/001* (2013.01);
(Continued)

(58) Field of Classification Search
CPC ............ B01J 19/0033; B01J 2219/0063; B01J 2219/00177; B01J 2219/00186; B01J 2219/002; G01N 21/82; G01N 21/253; G01N 21/53; G01N 1/32; G01N 33/442; G01N 21/05; G01N 2021/054; G01N 21/64; G01N 33/44; G01N 2021/4742; G01N 2021/4769; C08F 2/001; Y02P 20/582
(Continued)

(56) References Cited

U.S. PATENT DOCUMENTS 3,230,047 A 1/1966 Weinbrenner et al.
5,382,918 A 1/1995 Yamatake
(Continued)

FOREIGN PATENT DOCUMENTS

WO WO-03055919 A1 7/2003
WO WO-2008042870 A2 4/2008

OTHER PUBLICATIONS

Adebekun et al., Continuous solution polymerization reactor control. 2. Estimation and nonlinear reference control during methylmethacrylate polymerization. *Ind. Eng. Chem. Res.* 28: 1846-61 (1989).
(Continued)

*Primary Examiner* — William Cheung
(74) *Attorney, Agent, or Firm* — Marshall, Gerstein & Borun LLP

(57) ABSTRACT

A method of monitoring the evolution of polymer and/or colloid stimuli responsiveness during synthesis of polymers and/or colloids, including postpolymerization modifications on natural and synthetic polymers, includes providing a reactor in which the polymers and/or colloids are synthesized; and providing a means of monitoring the stimuli responsiveness of the polymers and/or colloids during said synthesis. Preferably, the method also includes monitoring the evolution of the characteristics of the polymers and/or colloids during said synthesis. Preferably, evolution of polymer and/or colloid stimuli responsiveness is correlated to the evolution of the properties of the polymers and/or colloids
(Continued)

themselves. Also, preferably the conditions of the fluid in the reactor in which the synthesis occurs is determined. The determination can be by detection, choice of materials and temperature conditions, for example, and combinations thereof. The method and instrumentation disclosed can lead to optimization and control of processes and synthetic and modification strategies leading to polymers and colloids with desired stimuli responsiveness.

29 Claims, 11 Drawing Sheets

Related U.S. Application Data

(60) Provisional application No. 61/059,050, filed on Jun. 5, 2008.

(51) Int. Cl.

| | |
|---|---|
| *G01N 33/00* | (2006.01) |
| *C40B 30/10* | (2006.01) |
| *G01N 33/44* | (2006.01) |
| *B01J 19/00* | (2006.01) |
| *G01N 21/25* | (2006.01) |
| *G01N 21/53* | (2006.01) |
| *G01N 21/82* | (2006.01) |
| *G01N 1/32* | (2006.01) |
| *G01N 21/05* | (2006.01) |
| *G01N 21/64* | (2006.01) |
| *G01N 21/47* | (2006.01) |
| *G01N 21/84* | (2006.01) |

(52) U.S. Cl.
CPC .............. *G01N 1/32* (2013.01); *G01N 21/253* (2013.01); *G01N 21/53* (2013.01); *G01N 21/82* (2013.01); *B01J 2219/002* (2013.01); *B01J 2219/00063* (2013.01); *B01J 2219/00177* (2013.01); *B01J 2219/00186* (2013.01); *G01N 21/05* (2013.01); *G01N 21/64* (2013.01); *G01N 33/44* (2013.01); *G01N 2021/054* (2013.01); *G01N 2021/4742* (2013.01); *G01N 2021/4769* (2013.01); *G01N 2021/8411* (2013.01); *Y02P 20/582* (2015.11)

(58) Field of Classification Search
USPC . 526/61, 60; 422/119; 436/106, 120; 506/12
See application file for complete search history.

(56) References Cited

U.S. PATENT DOCUMENTS

| | | | |
|---|---|---|---|
| 6,052,184 | A | 4/2000 | Reed |
| 6,618,144 | B1 | 9/2003 | Reed |
| 6,635,224 | B1 | 10/2003 | Gui et al. |
| 6,653,150 | B1* | 11/2003 | Reed .................. G01N 15/0211 436/164 |
| 7,716,969 | B2 | 5/2010 | Reed et al. |
| 8,198,880 | B2 | 6/2012 | Ouyang |
| 8,400,129 | B2 | 3/2013 | Ouyang |
| 8,686,703 | B2 | 4/2014 | Xi |
| 8,749,216 | B2 | 6/2014 | Li et al. |
| 2004/0004717 | A1 | 1/2004 | Reed |
| 2004/0115838 | A1 | 6/2004 | Quake et al. |
| 2006/0051818 | A1 | 3/2006 | Adriaenssens et al. |
| 2007/0128175 | A1 | 6/2007 | Ozbas et al. |
| 2008/0216563 | A1 | 9/2008 | Reed et al. |
| 2011/0273156 | A1 | 11/2011 | Miyamae |
| 2012/0235652 | A1 | 9/2012 | Sheng et al. |
| 2012/0235664 | A1 | 9/2012 | Dong et al. |
| 2012/0274293 | A1 | 11/2012 | Ren et al. |
| 2013/0002221 | A1 | 1/2013 | Wang et al. |
| 2013/0038301 | A1 | 2/2013 | Ouyang et al. |
| 2013/0038302 | A1 | 2/2013 | Qian et al. |
| 2013/0141069 | A1 | 6/2013 | Li |
| 2013/0147454 | A1 | 6/2013 | Wang |
| 2013/0257399 | A1 | 10/2013 | Jiang et al. |
| 2014/0022684 | A1 | 1/2014 | Jiang et al. |
| 2014/0035654 | A1 | 1/2014 | Jiang et al. |
| 2014/0049235 | A1 | 2/2014 | Li et al. |

OTHER PUBLICATIONS

Aerdts et al., Grafting of styrene and methyl methacrylate concurrently onto polybutadiene in semi-continuous emulsion processes and determination of copolymer microstructure. *Polymer* 35(8): 1648-53 (1994).

Alb et al., Automatic continuous online monitoring of polymerization reactions (ACOMP). *Polymer International*, 57(3): 390-6 (2008).

Alb et al., Evolution of composition, molar mass, and conductivity during the free radical copolymerization of polyelectrolytes. *J. Phys. Chem. B*, 111(29): 8560-6 (2007).

Alb et al., Kinetic trends in RAFT homopolymerization from online monitoring. *Macromolecules*, 41(2): 332-8 (2008).

Alb et al., Online monitoring of copolymerization involving comonomers of similar spectral characteristics. *Macromolecules*, 39(17): 5705-13 (2006).

Alb et al., Online monitoring of polymerization reactions in inverse emulsions. *Langmuir*, 22: 831-40 (2006).

Alb et al., Online monitoring of ring-opening metathesis of polymerization of cyclooctadiene and a functionalized norbornene. *Macromolecules*, 40(3): 444-51 (2007).

Alb et al., Quantitative contrasts in the copolymerization of acrylate- and methacrylate-based comonomers. *Macromolecules*, 39(24): 8283-92 (2006).

Alb et al., Recent advances in automatic continuous online monitoring of polymerization reactions (ACOMP). *Macromolecular Symposia*, 271(1): 15-25 (2008).

Alb et al., Simultaneous continuous, non-chromatographic and discrete chromatographic monitoring of polymerization reactions. *J. Appl. Polym. Sci.* 113: 190-8 (2009).

Alb et al., Simultaneous monitoring of polymer and particle characteristics during emulsion polymerization. *Macromolecules*, 41(7): 2406-14 (2008).

Alhamad et al., On-line multi-variable predictive control of molar mass and particle size distributions in free-radical emulsion copolymerization. *Chem. Eng. Sci.* 60(23): 6596-606 (2005).

Anantawaraskul et al., Cocrystallization of blends of ethylene/1-olefin copolymers: an investigation with crystallization analysis fractionation (crystaf). *Macromol. Chem. Phys.* 205(6): 771-7 (2004).

Anantawaraskul et al., Effect of operation parameters on temperature rising elution fractionation and crystallization analysis fractionation. *J. Polym. Sci. B: Polym. Phys.* 41(14): 1762-78 (2003).

Arehart et al., Atom transfer radical copolymerization of styrene and n-butyle acrylate. *Macromolecules*, 32(7): 2221-31 (1999).

Asua (ed.), Polymer Reaction Engineering, M. Oxford: Blackwell Publishing Ltd., 1-28 (2007).

Barner-Kowollik et al., Mechanism and kinetics of dithiobenzoate-mediated RAFT polymerization. I. The current situation. *J. Polym. Sci. Part A: Polym. Chem.* 44(2): 5809-31 (2006).

Bayly et al., Continuous monitoring of the effect of changing solvent conditions on polyelectrolyte conformations and interactions. *Int. J. of Polymer. Characterization and Analysis*, 7: 1-19 (2002).

Bielawskia et al., Living ring-opening metathesis polymerization. *Prog. Polym. Sci.* 32: 1-29 (2007).

Bowes et al., AB and ABA type butyl acrylate and styrene block copolymers via RAFT-mediated miniemulsion polymerization. *J. Polym. Sci. Part A: Polym. Chem.* 45(4): 588-604 (2007).

Braunecker et al., Controlled/living radical polymerization: Features, developments, and perspectives. *Prog. Polym. Sci.* 32(1): 93-146 (2007).

(56) References Cited

OTHER PUBLICATIONS

Britton et al., Effect of monomer feed rate on chain transfer to polymer in semibatch emulsion polymerization of vinyl acetate studied by NMR spectroscopy. *Macromolecules*, 33(14): 5048-52 (2000).
Butte et al., RAFT polymerization in bulk and emulsion. *Macromol. Symp.* 248(1): 168-81 (2007).
Cao et al., Molecular weight distribution of poly(methyl methacrylate) produced in a starved feed reactor. *J. Polym. Eng.* 21(5): 401-20 (2001).
Chang, Polymer characterization by interaction chromatography. *J. Polym. Sci. Part B: Polymer Physics*, 43(13): 1591-607 (2005).
Chauvin et al., Kinetics and molecular weight evolution during controlled radical polymerization. *Macromol. Chem. Phys.* 203: 2029-40 (2002).
Chern et al., Stability of carboxylated poly(butyl acrylate) latices during semibatch emulsion polymerization. *J. Appl. Polym. Sci.* 61(6): 989-1001 (1996).
Chien et al., Online sensors for polymerization reactors. *J. Macromol. Sci.—Reviews in Macromol. Chem. And Physics*, 1-42 (1990).
Chitanu et al., Static and dynamic light scattering of maleic acid copolymers. *Polymer*, 41(10): 3683-92 (2000).
Clay et al., Molecular weight distributions in free-radical polymerizations. 1. Model development in implications for data interpretation. *Macromolecules*, 28(2): 552-69 (1995).
Coady et al., Ionic dithioester-based RAFT agents derived from N-heterocyclic carbenes. *Macromolecules*, 41(11): 3775-8 (2008).
Coady et al., N-heterocyclic carbenes: versatile reagents for postpolymerization modification. *Macromolecules*, 39(26): 8895-7 (2006).
Colic et al., Electrophoretic behavior and viscosities of surfactant systems. *Colloid Polym. Sci.* 276(1): 19-26 (1998).
Congalidis et al., Feedforward and feedback control of a solution copolymerization reactor. *AIChE J.* 35(6): 891-907 (1989).
Dimitratos et al., Dynamic modeling and state estimation for an emulsion copolymerization reactor. *Comp. Chem. Eng.* 13: 21-33 (1989).
Drenski et al., Direct measurement of chain transfer during controlled radical polymerization. *Macromolecules*, 39(24): 8213-5 (2006).
Drenski et al., Simultaneous in situ monitoring of parallel polymerization reactions using light scattering; a new tool for high throughput screening. *J. Combinatorial Chemistry*, 6: 710-6 (2004).
Drenski et al., Simultaneous multiple sample light scattering for analysis of polymer solutions. *J. Appl. Polym. Sci.* 92(4): 2724-32 (2004).
Dube et al., A microcomputer program for estimation of copolymerization reactivity ratios. *J. Polym. Sci. Part A: Polym. Chem.* 29: 703-8 (1991).
Ellis et al., On-line molecular weight distribution estimation and control in batch polymerization. *AIChE J.* 40(3): 445-462 (1994).
Enohnyaket et al., Determination of molecular mass during online monitoring of copolymerization reactions. *Macromolecules*, 40(22): 8040-9 (2007).
Farinato et al., Online monitoring of the final divergent growth phase in the stepgrowth polymerization of polyamines. *Macromolecules*, 38: 1148-58 (2005).
Feldermann et al., An in-depth analytical approach to the mechanism of the RAFT process in acrylate free radical polymerizations via coupled size exclusion chromatography-electrospray ionization mass spectrometry (SEC-ESI-MS). *Polymer*, 46(19): 8448-57 (2005).
Feng et al., The measurement of compositional heterogeneity in a propylene-ethylene block copolymer. *Polymer*, 39(26): 6723-31 (1998).
Ferguson et al., Ab initio emulsion polymerization by RAFT-controlled self-assembly. *Macromolecules*, 38(6): 2191-204 (2005).
Ferguson et al., Effective ab initio emulsion polymerization under RAFT control. *Macromolecules*, 35(25): 9243-5 (2002).

Fevotte et al., Non-linear tracking of glass transition temperatures for free radical emulsion copolymers. *Chem. Eng. Sci.* 53(4): 773-86 (1998).
Florenzano et al., Absolute, on-line monitoring of molar mass during polymerization reactions. *Macromolecules*, 31(21): 7226-38 (1998).
Flores-Cerrillo et al., Control of particle size distributions in emulsion semibatch polymerization using mid-course correction policies. *Ind. Eng. Chem. Res.* 41(7): 1805-14 (2002).
Fujisawa et al., Copolymer composition control policies: characteristics and applications. *J. Macromol. Sci., Part A: Pure and Applied Chem.* 45(2): 115-32 (2008).
Garcia et al., Internal model control: a unifying review and some new results. *Ind. Eng. Chem. Process Design and Develop*, 21(2): 308-23 (1982).
Garcia et al., Monitoring the synthesis and properties of copolymeric polycations. *J. Phys. Chem. B*, 112(46): 14597-608 (2008).
Gattu et al., Nonlinear quadratic dynamic matrix control with state estimation. *Ind. Eng. Chem. Res.* 31(4): 1096-104 (1992).
Gerrens, On semicontinuous emulsion polymerization. *J. Polym. Sci. Part C*, 27(1): 77-93 (1969).
Ghielmi et al., Molecular weight distribution in emulsion polymerization: role of active chain compartmentalization. *Macromolecules*, 31(21): 7172-86 (1998).
Ghosh et al., Phase transitions in solutions of semiflexible polyelectrolytes. *J. Chem. Phys.* 116(12): 5299-307 (2002).
Giz et al., Kinetics and mechanism of acrylamide polyermization by absolute, online monitoring of polymerization kinetics. *Macromolecules*, 34(5): 1180-91 (2001).
Giz et al., Online monitoring of reactivity ratios, composition, sequence length and molecular weight distributions during free radical copolymerization. *Macromolecules*, 35(17): 6557-71 (2002).
Goto et al., Mechanism and kinetics of RAFT-based living radical polymerizations of styrene and methyl methacrylate. *Macromolecules*, 34(3): 402-8 (2001).
Grassi et al., Online polymerization monitoring in a continuous tank reactor. *Macromol. Chem. Phys.* 203: 586-97 (2002).
Hammouri et al., Applications of nonlinear observers and control: improving productivity and control of free radical solution copolymerization. *Ind. Eng. Chem Res.* 38: 4815-24 (1999).
Han et al., Synthesis of thermally sensitive water-soluble polymethacrylates by living anionic polymerizations of oligo(ethylene glycol) methyl ether methacrylates. *Macromolecules*, 36(22): 8312-9 (2003).
Hanley et al., Phase behavior of a block copolymer in solvents of varying selectivity. *Macromolecules*, 33(16): 5918-31 (2000).
Henson, Nonlinear model predictive control: current status and future directions. *Comp. Chem. Eng.* 23(2): 187-202 (1998).
Heredia et al., Aminooxy end-fucntionalized polymers synthesized by ATRP for chemoselective conjugation to proteins. *Macromolecules*, 40(14): 4772-9 (2007).
Hur et al., Design and application of model-on-demand predictive controller to a semibatch copolymerization reactor. *Ind. Eng. Chem. Res.* 42(4): 847-59 (2003).
Kammona et al., Recent developments in hardware sensors for the on-line monitoring of polymerization reactions. *J. Macromol. Sci.—Reviews in Macromol. Chem.* 39: 57-134 (1999).
Kim et al., Amphiphilic diblock copolymers based on poly(2-ethyl-2-oxazoline) and poly(1,3-trimethylene carbonate): synthesis and micellar characteristics. *Macromolecules*, 33: 7448-52 (2000).
Kim et al., Surface rheology of monolayers of triblock copolymers of PEO and PPO: surface light scattering studies at the air/water surface. *Langmuir*, 19(10): 4460-64 (2003).
Kiparissides et al., Intelligent manufacturing of polymers. *Comp. Chem. Eng.* 20(Suppl.): S1113-8 (1999).
Kozub et al., State estimation for semi-batch polymerization reactors. *Chem. Eng. Sci.* 47(5): 1047-62 (1992).
Krackeler et al., Particle size and molecular weight distributions of various polystyrene emulsions. *Polym. Sci. Part C*, 27(1): 207-35 (1969).

(56) References Cited

OTHER PUBLICATIONS

Kramer et al., Chemical heterogeneity analysis of high-conversion poly(styrene-co-(ethylacrylate))s by NMR and online coupled SEC-NMR. *Macromol. Chem. Phys.* 200(7): 1734-44 (1999).

Kravaris et al., Nonlinear controllers for trajectory tracking in batch processes. *Comp. Chem. Eng.* 13: 73-82 (1989).

Kreft et al., Direct monitoring of the cross-over from the diffusion-controlled to decomposition-controlled initiation in free radical polymerization. *Macromol. Chem. Phys.* 209(24): 2463-74 (2008).

Kreft et al., Experimental observation of cross-over from non-condensed to counterion condensed regimes during free radical polyelectrolyte copolymerization under high composition drift conditions. *J. Phys. Chem. B.* 113: 8303-9 (2009).

Kreft et al., Predictive control and verification of conversion kinetics and polymer molecular weight in semi-batch free radical homopolymer reactions. *European Polymer J.* 45: 2288-303 (2009).

Kreft et al., Predictive control of average composition and molecular weight distributions in semibatch free radical copolymerization reaction. *Macromolecules*, 42 (15): 5558-65 (2009).

Lambeth et al., Synthesis and aggregation behavior of thermally responsive star polymers. *Langmuir*, 22(14): 6352-60 (2006).

Lee et al., Extended Kalman filter based nonlinear model predictive control. *Ind. Eng. Chem. Res.* 33(6): 1530-41 (1994).

Lodge et al., Origins of anomalous micellization in diblock copolymer solutions. *Langmuir*, 19(6): 2103-9 (2003).

Lodge, Block Copolymers: past successes and future challenges. *Macromol. Chem. Phys.* 204(2): 265-73 (2003).

Ludwigs et al., Phase behavior of linear polystyrene-block-poly(2-vinylpyridine)-block-poly(tert-butyl methacrylate) triblock terpolymers. *Polymer*, 44(22): 6815-23 (2003).

Luo et al., Cellular internalization of poly(ethylene oxide)-b-poly(e-caprolactone) diblock copolymer micelles. *Bioconjugate Chem.* 13(6): 1259-65 (2002).

Lutz et al., Polymerization of oligo(ethylene glycol) (meth)acrylates: Toward new generations of smart biocompatible materials. *J. Polym. Sci. Part A: Polym. Chem.* 46(1): 3459-70 (2008).

Mao et al., High-throughput studies of the effects of polymer structure and solution components on the phase separation of thermoresponsive polymers. *Macromolecules*, 37: 1031-6 (2004).

Martins dos Santos et al., Combining steric and electrostatic stabilization using hydrophilic macroRAFT agents in an ab initio emulsion polymerization of styrene. *Macromol. Rapid Commun.* 28(12): 1325-32 (2007).

Matyjaszewski et al. (ed.), Controlled/living radical polymerization. Progress in ATRP, NMP, and RAFT, *ACS Symp. Ser.* 768: 2-26 (2000).

Maynard et al., Synthesis of functionalized polyethers by ring-opening metathesis polymerization of unsaturated crown ethers. *Macromolecules*, 32(21): 6917-24 (1999).

Maynard et al., Thermoresponsive biohybrid materials synthesized by ATRP. *J. Mat. Chem.* 17: 4015-7 (2007).

Mayo et al., Copolymers I, a basis for comparison the behavior of monomers in copolymerization. *J. Am. Chem. Soc.* 66: 1594-1601 (1944).

McKenna et al., Joint use of calorimetry, densimetry and mathematical modeling for multiple component polymerizations. *Chem. Eng. Res. & Design*, 74(3): 340-8 (1996).

McLeary et al., RAFT mediated polymerization in heterogeneous media. *Soft Matter*, 2(1): 45-53 (2006).

Meehan et al., Characterization of block-copolymers using size-exclusion chromatography with multiple detectors. *Adv. Chem. Ser.* 247: 243-51 (1995).

Mignard et al., Kinetics and molar mass evolution during atom transfer radical polymerization of n-butyl acrylate using automatic continuous online monitoring. *Macromolecules*, 38: 9556-63 (2005).

Mignard et al., Online monitoring of controlled radical polymerization: Nitroxide mediated gradient copolymerization. *Macromolecules*, 37: 966-75 (2004).

Moad et al., Living radical polymerization by the RAFT process—a first update. *Aust. J. Chem.* 59(10): 669-92 (2006).

Moran et al., Model predictive control: Theory and practice-A survey. *Automatica*, 25(3): 335-48 (1989).

Mori, Determination of chemical composition and molecular weight distributions of high-conversion styrene-methyl methacrylate copolymers by liquid adsorption and size exclusion chromatography. *Analyt. Chem.* 60(11): 1125-8 (1988).

Munoz-Bonilla et al., Synthesis and aqueous solution properties of stimuli-responsive triblock copolymers. *Soft Matter*, 3(6): 725-31 (2007).

Mutha et al., A new multirate-measurement-based estimator: emulsion copolymerization batch reactor case study. *Ind. Eng. Chem. Res.* 36(4): 1036-47 (1997).

Mutha et al., On-line nonlinear model-based estimation and control of a polymer reactor. *AIChE J.* 43(11): 3042-58 (1997).

Narrainen et al., Amphiphilic diblock, triblock, and star block copolymers by living radical polymerization: Synthesis and aggregation behavior. *J. Polym. Sci. Part A: Polym. Chem.* 40(4): 439-50 (2002).

Netopilik et al., Influence of chemical heterogeneity of copolymers on the separation process on size-exclusion chromatography. *Macromolecules*, 29(18): 6023-30 (1996).

Nicolas et al., Fluorescently labeled protein-polymer bioconjugates using protein-derived macroinitiators from living radical polymerization. *Polymers for Biomedical Applications*, 977: 78-94 (2008).

Norwood et al., Comparison of on-line single-capillary and bridge capillary viscometric detectors for size exclusion chromatography. *Int. J. Polym. Ana. and Char.* 4(2): 99-132 (1997).

Novak, Mechanism of acrylic emulsion polymerizations. *Adv. Org. Coat Sci. Technol. Ser.* 10: 54-7 (1988).

Othman et al., Control of polymer molecular weight using near infrared spectroscopy. *AIChE J.* 50(3): 654-64 (2004).

Othman et al., On-line monitoring and modeling of free radical copolymerisations: butyl acrylate/vinyl acetate. *Polym. React. Eng.* 7(1): 1-42 (1999).

Paril et al., Online monitoring of the evolution of polyelectrolyte characteristics during postpolymerization modification processes. *Macromolecules*, 40: 4409-13 (2007).

Park et al., Control of copolymer properties in a semibatch mthyl mathacrylate/methyl acrylate copolymerization reactor by using a learning-based nonlinear model predictive controller. *Ind. Eng. Chem. Res.* 43(11): 2736-46 (2004).

Parouti et al., A comprehensive experimental investigation of the methyl methacrylate/butyl acrylate/acrylic acid emulsion terpolymerization. *Polym. React. Eng.* 11(4): 829-53 (2003).

Patton et al., A versatile synthetic route to macromonomers via RAFT polymerixzation. *Macromolecules*, 39(25): 8674-83 (2006).

Pergushov et al., Micelles of polyisobutylene-block-poly(methacrylic acid) diblock copolymers and their water-soluble interpolyelectrolyte complexes formed with quaternized poly(4-vinylpyridine). *Polymer*, 45(2): 367-78 (2004).

Pham et al., Miniemulsion polymerization stabilized by amphipathic macro RAFT agents. *Macromolecules*, 36(24): 8907-9 (2003).

Philipsen, Determination of chemical composition distributions in synthetic polymers. *J. Chromatography*, 1037(1-2): 329-50 (2004).

Pichot et al., Functionalized thermosensitive latex particles useful tools for diagnostics. *J. Dispers. Sci. Technol.* 24(3-4) 423-37 (2003).

Pichot, Surface-functionalized latexes for biotechnological applications. *Current Opinion in Colloid & Interface Sci.* 9(3-4): 213-21 (2004).

Pitsikalis et al., Block copolymers of styrene and stearyl methacrylate. Synthesis and micellization properties in selective solvents. *Macromolecules*, 33(15): 5460-9 (2000).

Plamper et al., Nanoblossoms: light-induced conformational changes of cationic polyelectrolyte stars in the presence of multivalent counterions. *Nano Lett.* 7(1): 167-71 (2007).

Plessis et al., Modeling of seeded semibatch emulsion polymerization of n-BA. *Ind. Eng. Chem. Res.* 40(18): 3883-94 (2001).

(56) References Cited

OTHER PUBLICATIONS

Puskas et al., Kinetics and mechanisms in carbocationic polymerization: the quest for true rate constants. *J. Polym. Sci., Chem.* 43(22): 5394-413 (2005).
Puskas et al., Real-time FTIR monitoring of the carbocationic copolymerization of isobutylene with styrene. *Macromol. Chem. Macromol. Symp.* 240(1): 18-22 (2006).
Qin et al., A survey of industrial model predictive control technology. *Control Eng. Practice* 11(7): 733-64 (2003).
Qiu et al., Emulsion polymerization of n-butyl methacrylate by reverse atom transfer radical polymerization. *Macromolecules*, 32(9): 2872-5 (1999).
Richalet et al., Model predictive heuristic control ☆: Applications to industrial processes. *Automatica*, 14(5): 413-28 (1978).
Richards et al., Measurement and control of polymerization reactors. *Comp. Chem. Eng.* 30(10-12): 1447-63 (2006).
Sajjadi et al., Semibatch emulsion polymerization of butyl acrylate. II. Effects of emulsifier distribution. *J. Appl. Polym. Sci.* 79(4): 582-97 (2001).
Sajjadi, Nanoparticle formation by monomer-starved semibatch emulsion polymerization. *Langmuir*, 23(3): 1018-24 (2007).
Sajjadi, Particle formation under monomer-starved conditions in the semibatch emulsion polymerization of styrene. I. Experimental. *J. Polym. Sci., Polym. Chem. Ed.* 39(22): 3940-52 (2001).
Sauzedde et al., Determination of the composition of statistical copolymers by liquid chromatography under limiting conditions of adsorption. *Int. J. Polym. Anal. Charact.* 6(3-4): 295-314 (2001).
Save et al., Controlled radical polymerization in aqueous dispersed media. *Australian J. Chem.* 59(10): 693-711 (2006).
Sayer et al., Kinetics of the seeded semicontinuous emulsion copolymerization of methyl methacrylate and butyl acrylate. *Polym. Sci. Part A: Polym. Chem.* 38(2): 367-75 (2000).
Seo et al., Study on the behaviors of different polystyrene-block-poly(methyl methacrylate) diblock copolymers adsorbed at the air/water interface. *Langmuir*, 19(8): 3313-22 (2003).
Shaikh et al., A new high-throughput approach to measure copolymerization reactivity ratios using real-time FTIR monitoring. *J. Polym. Sci. Part A: Polym. Chem.* 42(16): 4084-100 (2004).
Shaw et al., Simulating joint chain length and composition fraction from semi-batch ethylene copolymerization experiments. *Polym. React. Eng.* 6(2): 113-42 (1998).
Simms et al., Xanthate-mediated living radical polymerization of vinyl acetate in miniemulsion. *Macromol. Rapid Commun.* 26(8): 592-6 (2005).
Sorci et al., Effect of ion type and valence on polyelectrolyte conformations and interactions. *Macromolecules*, 37(2): 554-65 (2004).
Sorci et al., Electrostatically enhanced second and third virial coefficients, viscosity, and interparticle correlations for linear polyelectrolytes. *Macromolecules*, 35(13): 5218-27( 2002).
Stockmayer, Distribution of chain length and compositions in copolymers. *J. Chem. Phys.* 13: 199-207 (1945).
Sun et al., Programmed synthesis of copolymer with controlled chain composition distribution via semibatch RAFT copolymerization. *Macromolecules*, 40(4): 849-59 (2007).
Tacx et al., Determination of molar-mass chemical-composition distribution in copolymers by cross-fractionation, based on size exclusion chromatography and thin-layer chromatography/flame ionization detection. *Polymer*, 30(5): 918-27 (1989).
Taranekar et al., Conjugated polymer nanoparticles via intramolecular crosslinking of dendrimeric precursors. *Adv. Mater.* 18(18): 2461-5 (2006).
Taranekar et al., Structure and band-gap design of a new series of light emitting poly(cyanofluorene-alt-o/m/p-phenylenevinylene)-based copolymers for light-emitting diodes. *Macromolecules*, 39(11): 3848-54 (2006).
Theis et al., Probing the reaction kinetics of vinyl acetate free radical polymerization via living free radical polymerization (MADIX). *Polymer*, 47(4): 999-1010 (2006).
Tobita et al., Bivariate distribution of chain length and composition in multicomponent polymerization. *Polymer*, 39(11): 2367-72 (1998).
Tusa et al., Fluorescence Studies of pH-responsive unimolecular micelles formed from amphiphilic polysulfonates possessing long chain alkyl carboxyl pendants. *Macromolecules*, 35(27): 10182-8 (2002).
Van den Dungen et al., Investigation into the initialization behavior of RAFT-mediated styrene-maleic anhydride copolymerizations. *Aust. J. Chem.* 59(10): 742-8 (2006).
Vicente et al., Dynamic optimization of non-linear emulsion copolymerization systems: Open-loop control of composition and molecular weight distribution. *Chem. Eng. J.* 85(2-3): 339-49 (2002).
Vicente et al., Simultaneous control of copolymer composition and MWD in emulsion copolymerization. *AIChE J.* 47(7): 1594-606 (2001).
Wang et al., Design and control of copolymer composition distribution in living radical polymerization using semi-batch feeding policies: a model situation. *Macromol. Theory Simul.* 15(4) 356-68.
Wessling, Kinetics of continuous addition emulsion polymerization. *J. Appl. Polym. Sci.* 12(2): 309-19 (1968).
Wiesbrock et al., New challenges in combinatorial polymer research: 3rd DPI workshop on automated synthesis and high-throughput experimentation in polymer and materials research at the Eindhoven University of Technology. *Macromolecular Rapid Communications*, 25(17): 1579-82 (2004).
Wild, Temperature rising elution fractionation. *Adv. Polym. Sci.* 98: 1-47 (1991).
Winnik et al. (eds.), Stimuli-responsive materials: polymers, colloids, and multicomponent systems. *Langmuir*, 23(1): 1-2 (2007).
Wu et al., Kinetic and molecular weight control for methyl methacrylate semi-batch polymerization. I. Modelling. *J. Appl. Polym. Sci.* 100(4): 2838-46 (2006).
Yanjarappa et al., Synthesis of copolymers containing an active ester of methacrylic acid by RAFT: controlled molecular weight scaffolds for biofunctionalization. *Biomacromolecules*, 7(5): 1665-70 (2006).
Yusa et al., Fluorescence studies of pH-responsive unimolecular micelles formed from ampihilic plysulfonates possessing long-chain alkyl carboxyl pendants. *Macromolecules*, 35(27): 10182-288 (2002).
Zacur et al., Dispersed phase morphology of impact PP copolymers. Effects of blend composition as determined by TREF. *Polymer Sci. Eng.* 40(8): 1921-30 (2000).
Zhang et al., Effects of Hofmeister anions on the LCST of PNIPAM as a function of molecular weight. *J. Phys. Chem. C. Nanomater. Interfaces*, 111(25): 8916-24 (2007).
Zhao et al., Fluorescence probe techniques used to study micelle formation in water-soluble block copolymers. *Langmuir*, 6(2): 514-6 (1990).

\* cited by examiner

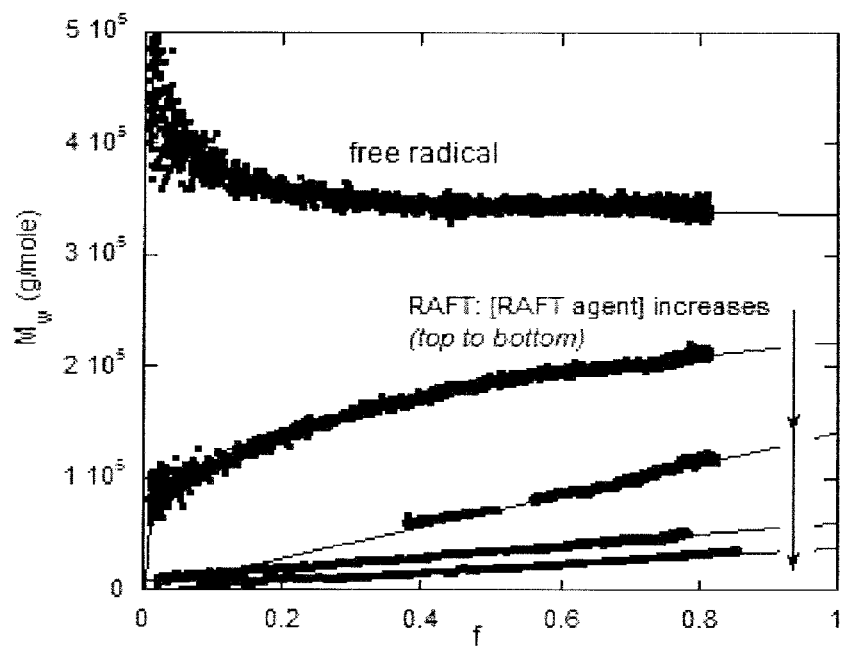
FIG. 11
FIG. 12
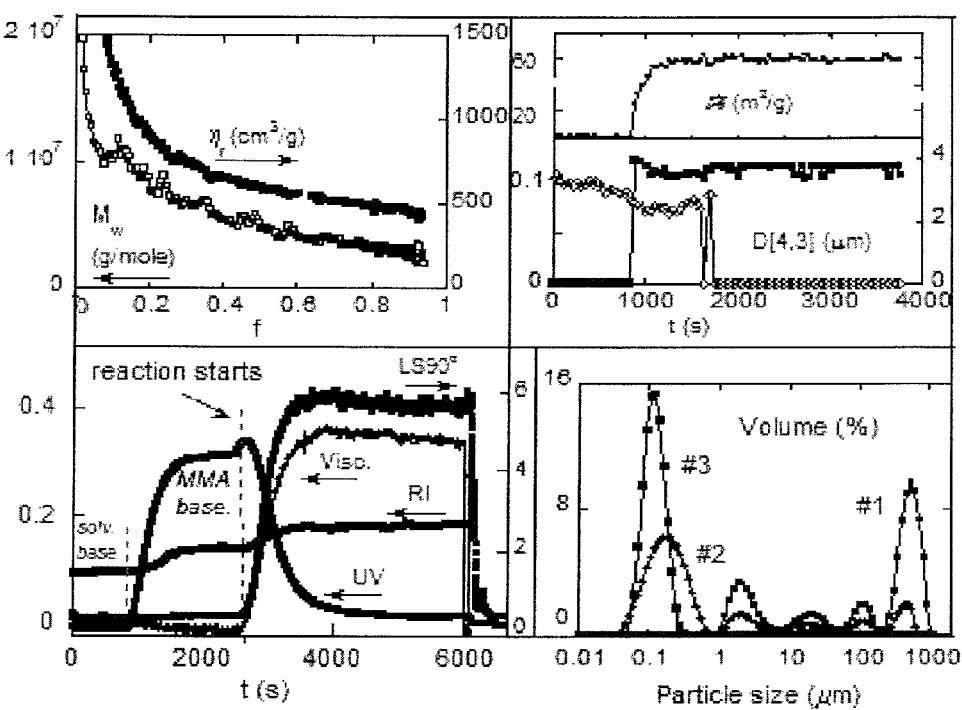

METHODS AND INSTRUMENTATION FOR DURING-SYNTHESIS MONITORING OF POLYMER FUNCTIONAL EVOLUTION

CROSS-REFERENCE TO RELATED APPLICATIONS

This U.S. Patent application is a continuation of U.S. patent application Ser. No. 12/479,052, filed 5 Jun. 2009, which claims priority to U.S. Provisional Patent Application Ser. No. 61/059,050, filed 5 Jun. 2008. Each specification of the foregoing applications is hereby incorporated by reference in its entirety.

U.S. patent application Ser. No. 11/865,589, filed 1 Oct. 2007, and International Application Number PCT/US2007/80116, filed 1 Oct. 2007, are hereby incorporated herein by reference.

U.S. Provisional Patent Application Ser. No. 60/827,559, filed 29 Sep. 2006, and U.S. Provisional Patent Application Ser. No. 60/884,821, filed 12 Jan. 2007, are hereby incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a 'second generation of ACOMP' (Automatic Continuous Online Monitoring of Polymerization reactions). The present document also sets out principles and uses, for the first time, of ACOMP (U.S. Pat. No. 6,653,150) coupled to SMSLS (simultaneous multiple sample light scattering, a Reed patent (U.S. Pat. No. 6,618,144) held by Tulane), and expands the uses of SMSLS through specific design changes.

The present invention is particularly suited to monitoring special characteristics of polymers and colloids as they evolve during reactions, such as polymer synthesis or post-polymerization modification reactions. Special characteristics include the polymers' and/or colloids' ability to respond to environmental stimuli, such as temperature, light, and solution characteristics such as pH, ionic strength, presence of specific other substances, such as toxins, drugs, surfactants, and other molecules, including other polymers, colloids, and nanostructures, their ability to go through structural changes, such as conformational collapse, their ability to self-assemble into supramolecular structures, and their ability to encapsulate and bind other agents, and to release them. The use of the present invention in conjunction with multiple similar detectors in some contexts can allow determination of polymer and/or colloid phase behavior during reactions, and how the phase behavior changes during reactions.

Although the samples are prepared automatically and continuously, detection can be intermittent. Interrupted, chromatographic detection, such as size exclusion chromatography, can be used. A recent publication the inventor and his colleagues made in this area is: "Simultaneous continuous, non-chromatographic monitoring and discrete chromatographic monitoring of polymerization reactions", Alina M. Alb, Michael F. Drenski, Wayne F. Reed, J. Appl. Polym. Sci., 13, 190-198, 2009. A stop-flow method is also described below.

2. General Background of the Invention

As polymers become more complex and sophisticated in architecture and composition, they gain the ability to perform more 'intelligent' functions than traditional polymers. The frontier of advanced polymeric materials in the 21st century will be dominated by these increasingly sophisticated polymers. The upcoming polymers can micellize, aggregate, and respond to stimuli, such as temperature, light, solvent polarity, different solvents and solvent mixtures, the presence of specific agents, metal ions, surfactants, multi-valent ions, proteins, anti-bodies, receptors, etc. (see Langmuir (2007), 23, 1, 1-2; Polymer (2004), 45(2), 367-378; Macromolecular Chemistry II, University of Bayreuth, Bayreuth, Germany. Abstracts of Papers, 235th ACS National Meeting, New Orleans, La., United States, Apr. 6-10, 2008 (2008), POLY-599; Nano letters (2007), 7(1), 167-71; Journal of Materials Chemistry (2007), 17(38), 4015-4017; Langmuir, (1990), 6, 514-516; Macromolecules (2002), 35, 10182-10288; J. Phys. Chem. C (2007), 111, 8916-8924). The polymers and/or colloids may also undergo chemical reactions with other species.

Applications include sensing, encapsulation and release of agents (e.g. drugs, cosmetics, etc.), micropatterning, bioconjugated polymers for medical applications, self-healing, photosensitivity and/or electrically conductive properties for optical and electronics applications, photovoltaics etc. There is considerable interest in 'fine tuning' polymers to have well behaved stimuli responsiveness characteristics, interaction properties, specific phase behavior, etc.

Henceforth 'stimuli responsiveness' will be used to refer to one or more of the diverse types of behaviors that polymers and/or colloids can manifest, depending on their own structure, composition and other macromolecular and chemical characteristics, the conditions of their synthesis, and the details of the environment where they may be synthesized, transferred to, or otherwise used or applied. Such behaviors can include but are not limited to conformational changes, intra- and/or intermolecular micellization, intermolecular aggregation and/or supramolecular assemblage into organized structures, solubility, phase separation, ability to interact with other polymers or colloids or small molecules, such as metal ions, organic molecules, salts, surfactants, etc., ability to no longer interact with certain substances, ability to encapsulate and/or release drugs and other biologically active agents, lower critical solution temperature (LCST), color changes, and ability to react chemically with other species.

For example, polymers in solution can acquire stimuli responsiveness in sharp or gradual ways; e.g. LCST (lower critical solution temperature), micellization, aggregation, helix-coil, and other intra- and intermolecular transitions. Such transitions are of fundamental and applied interest. Fundamentally, they arise from the thermodynamics of complex, interacting systems. Whether sharp or gradual, these transitions, and stimuli responsiveness in general, depend on many factors, such as pH, ionic strength, solvent type and polarity, solvent mixture types, solvent chaotropicity or cosmotropicity, temperature, irradiation by electromagnetic waves, including light, and addition of interacting agents (e.g. small molecules, dyes, etc.), as well as the molecular weight and copolymeric composition and microstructure of the polymers themselves. Other examples concern the many types of associations that can take place between polymers and other polymers, micelles, emulsions, vesicles, liposomes, proteins, polypeptides, etc. These often involve formation of supramolecular (non-covalent) structures promoted by electrostatic, hydrophobic, depletion, and other forces.

Another very important application for the present invention is in the field of polymers derived from natural products. Because of the increasing demand for renewable sources for polymeric materials, as well as biodegradability and environmental concerns, there is a growing number of natural products that are being used for medicine, food, cosmetics, water treatment, oil recovery, composite materials, etc. These include, but are not limited to polysaccharides such as xanthans, alginates, cellulose derivatives, chitin derivatives, galactomannans, pectins, etc. as well as proteins and fibers. In order to make use of these natural products it is necessary to extract the desired agents, and then often modify them chemically, enzymatically, or by radiation, until desired characteristics are obtained, such as solubility in a given solvent (e.g. water), ability to interact with other substances (e.g. surfactants), achieve desired levels of viscosification, self-assemble into nano and microstructures, etc. The present invention will allow all of these processes-extraction, modification, and special properties- to be monitored. This will allow for optimization of the processes used in extracting, modifying, and deploying natural product derived polymers and colloids. The ability to monitor and control these steps is particularly important for natural products because the raw material, of vegetable or animal origins are normally highly variable in the content and characteristics of the desired materials to be extracted, which is a perennial problem for natural product manufacturers.

'Polymer and/or colloid synthesis' includes any type of reaction in which a polymer and/or colloid is produced or modified. An example of the latter is when a polymer is first made and then specific functional groups are attached to it, such as charge groups (e.g. sulfate, quaternary amines, carboxylate, etc.), oligomers, grafted polymers, etc. Other examples include the modifications made to polymers and/or colloids extracted from natural biological sources (e.g. plants, wood, seeds, fruits, etc.), as described above.

Traditional Methods for Relating Polymer Characteristics to their Stimuli Responsiveness.

These are time-consuming, cumbersome, and inefficient. They normally involve, even in modern high-throughput systems, the synthesis of a given end-product, or series of end-products, that are then subjected to various types of functionality characterization, and often also to standard polymer characterization methods. In many cases, the mere preparation of the endproduct can be disproportionately time-consuming, and require such steps as precipitation, purification, freeze-drying, re-dissolution, dialysis, etc., of the end-product. The usual ACOMP approach, (see W. F. Reed, U.S. Pat. No. 6,653,150, "Automatic mixing and dilution methods for online characterization of equilibrium and non-equilibrium properties of solutions containing polymers and/or colloids"; and A. M. Alb, M. F. Drenski, W. F. Reed, "Automatic continuous online monitoring of polymerization reactions (ACOMP)", Polymer International, 57, 390-396, 2008) which has proven successful in a wide variety of contexts avoids these process steps by substituting 'fluid-fluid' sample handling. That is, the reactor fluid is continuously extracted, diluted with other fluids, and conditioned to produce a continuously measurable fluid sample of the reactor contents. No intermediate solid phase stages are normally used, and the often high levels of dilution (ranging up to dilution factors of many thousands) can even effectively change solvents by making the original solvent a tiny admixture to the dilution solvent. Such extraction/dilution/conditioning typically occurs on a time scale of tens of seconds to several minutes. The series of handling procedures in traditional methods can take hours, days, and even weeks.

The following references, and all references mentioned herein, are incorporated herein by reference:
Some additional bibliography showing LCST, micellization, bioconjugation, etc.:
Macromolecular Chemistry II, University of Bayreuth, Bayreuth, Germany. Abstracts of Papers, 235th ACS National Meeting, New Orleans, La., United States, Apr. 6-10, 2008 (2008), POLY-599. Publisher: American Chemical Society, Washington, D.C.;
Abstracts of Papers, 233rd ACS National Meeting, Chicago, Ill., United States, Mar. 25-29, 2007 (2007);
Polymer (2003), 44(22), 6815-6823;
Polymer Preprints (American Chemical Society, Division of Polymer Chemistry) (2003), 44(1), 646-647;
Abstracts of Papers, 235th ACS National Meeting, New Orleans, La., United States, Apr. 6-10, 2008 (2008), POLY-596;
ACS Symposium Series (2008), 977 (Polymers for Biomedical Applications), 78-94. Publisher: American Chemical Society;
Soft Matter (2007), 3(6), 725-731;
Macromolecules (Washington, D.C., United States) (2007), 40(14), 4772-4779;
Abstracts of Papers, 231st ACS National Meeting, Atlanta, Ga., United States, Mar. 26-30, 2006 (2006), PMSE-224;
Macromolecules (1999), 32(21), 6917-6924;
Polymer Preprints (American Chemical Society, Division of Polymer Chemistry) (2002), 43(2), 969-970
PMSE Preprints (2002), 87 237-238. Publisher: American Chemical Society, CODEN: PPMRA9 ISSN: 1550-6703. Journal; Computer Optical Disk written in English.

BRIEF SUMMARY OF THE INVENTION

Methods and instrumentation are disclosed for monitoring how polymer stimuli responsiveness evolves during the very process of polymer synthesis. Polymer stimuli responsiveness includes the ability of polymers, when certain characteristics are reached (e.g. molecular weight, composition, degree of postpolymerization modification etc.), to go through phase changes (e.g. micellization, formation of supramolecular structures), conformational changes, solubility changes, and other transformations (e.g. ability to interact with other polymers, or chemical or biochemical agents), often dependent on solution conditions (e.g. temperature, pH, ionic strength, specific electrolyte content, etc.). A new generation of polymers is being designed with high stimuli responsiveness for diverse purposes such as biomedical assays, drug delivery, sensing, responsiveness to stimuli (e.g. heat, light, etc.), self-healing materials, and much more.

The current invention offers a way of monitoring the evolution of stimuli responsiveness in a continuous way, during polymer synthesis. 'Polymer synthesis' includes any type of reaction in which a polymer is produced or modified. An example of the latter is when a polymer is first made and then specific functional groups are attached to it, such as charge groups (e.g. sulfate, quaternary amines, carboxylate, etc.), oligomers, grafted polymers, etc. In its simplest form the present invention is already a high throughput screening platform. In its enhanced form, described below, the present invention becomes a 'high throughput squared' platform, and may challenge and even disrupt ongoing high throughput developments that use expensive, robotic, multi-reactor approaches for mere end product analysis.

The current invention builds on Tulane's patent estate developed by Wayne F. Reed (U.S. Pat. Nos. 6,052,184, 6,653,150, 6,618,144, others pending), and preferred embodiments of the present invention advantageously use the teachings of some of those same patents (U.S. Pat. Nos. 6,052,184, 6,653,150, 6,618,144, others pending).

The present invention builds on the present inventor's last decade of invention and development in monitoring polymerization reactions, denoted as the ACOMP platform (Automatic Continuous Online Monitoring of Polymerization reactions). That work extended ACOMP's reach to free radical and controlled radical homo- and copolymerization, other 'living' reactions, condensation polymerization, branching, grafting, copolymeric polyelectrolyte synthesis, and polymer modification processes, including postpolymerization modifications and modifications of natural products, in homogeneous, bulk, and emulsion phase, and in batch, semi-batch and continuous reactors, producing corresponding discoveries in fundamental reaction kinetics and mechanisms.

With its broad range of monitoring applicability now secured, the present invention is a '$2^{nd}$ generation ACOMP' as it faces wholly new challenges; moving beyond monitoring to reaction control in order to produce polymers of desired characteristics, and extending the ACOMP platform to monitor, understand and control, the stimuli-responsiveness of polymers. These latter include polymers whose properties change with changing environmental factors, such as temperature, light, pH, solvent quality, presence of specific molecules, etc. The potential applications of these materials make them an exciting interface between chemical and biomolecular engineering, chemistry, materials science, and physics.

The discovery and development of new polymers require sophisticated analytical approaches that can solve basic and applied problems, and optimize processes. Currently, post-synthetic analyses on end-products with techniques such as size exclusion chromatography (SEC), nuclear magnetic resonance (NMR), etc. yield little information on the evolution of polymer characteristics and there is no opportunity for control. Utilizing a flexible detection platform that continuously or substantially continuously monitors reactions (e.g. light scattering, viscosity) ACOMP follows conversion kinetics, composition drift, and the evolution of average composition distribution, molar mass, and intrinsic viscosity distributions. The polymer is hence 'born' characterized, and there is also the opportunity for reaction control, a primary focus of the proposed work. The onset or change of stimuli responsiveness, such as conformational transformations, ability to interact with target molecules, copolymer micellization, etc. have complex relationships to polymer mass, architecture, and copolymer distribution, 'blockiness', sequence length distributions, etc. This work takes the novel approach of monitoring the onset of stimuli responsiveness during synthesis, focusing on lower critical solution temperature (LCST), with the subsequent ability for control, providing a powerful new tool for understanding underlying polymer physics and manipulating polymer structure/function relationships.

The present inventor aims to create a paradigm shift in polymer science, in which online monitoring and control become powerful adjuncts to polymer discovery, development and production, and for understanding stimuli responsive behavior in polymer solutions. Importantly, information-rich ACOMP results also provide a more complete database, and are available for polymer scientists in the broader community involved in modeling and reaction engineering. It is expected that the present invention will also quickly have real economic impact on polymer industries, yielding practical new materials and process monitoring and control that enhance savings of energy, petroleum, and other non-renewable resources, plant and labor time, and lead to better safety, and less greenhouse gas emissions and environmental pollution per kilogram of product.

The present invention includes a multi-purpose, multi-user $2^{nd}$ generation ACOMP instrument (Automatic Continuous Online Monitoring of Polymerization reactions). The present invention has an even more massive data gathering and analysis capability than its predecessors.

The multi-purpose platform of the present invention allows different time-dependent processes in polymer and colloid solutions to be monitored, and also can be used to automatically map characteristics of multi-component solutions in equilibrium or quasi-equilibrium, such as automatic determination of phase diagrams, and combines sophisticated, interconnected optical detection methods, and a fully integrated multi-detector GPC.

A few features and types of processes to be monitored are outlined below.

Simultaneous monitoring of polymer properties, such as mass and composition, and the onset of stimuli responsiveness during synthesis (including any postpolymerization modifications), such as phase transitions, micellization, conformational changes, microgelation, ability to interact with other substances, such as drugs, etc. The SG-ACOMP will be the only instrument of its kind in the world, able to determine at what point in synthesis, (including postpolymerization reactions and modifications of polymers and colloids extracted from natural products), polymers and copolymers become stimuli responsive, whether sharply or gradually; e.g. the effect of solvent type on LCST (lower critical solution temperature) of an evolving polymer and the relationship with polymer composition and molecular weight distributions could be determined. The transition at the LCST will be automatically detected, and the threshold characteristics of the polymer stimuli responsiveness can be quantified.

High throughput capability for testing stimuli responsiveness of polymers during synthesis. This portion of the system makes use of multiple light scattering and other detectors, built according to the concept of one of Reed's earlier patents; SMSLS (Simultaneous Multiple Static Light Scattering). This allows for a plurality of independent SMSLS flow cells to simultaneously measure a highly diluted polymerization sample stream under different conditions; e.g. temperature, solvent ionic strength and dielectric constant, etc.

Other optical detectors will allow for numerous other measurements, including dynamic light scattering, depolarized light scattering, Mie scattering, circular dichroism, UV/visible spectroscopy, fluorescence, and birefringence. Depolarized light scattering will allow anisotropic particles (e.g. nanotubes, rigid nano fibers, bacteria, etc.) to be analyzed.

The entire system can be used with multi-detector GPC in series or in stand-alone mode. Other functions can be switched modularly into the data gathering base, and also separately used.

Applications to biomedical fields, including drug delivery. Core-shell micellization and phase transition of copolymers will be continuously monitored. Amphiphilic block copolymers that self-assemble into micelles in aqueous media can be extensively investigated and their properties of 'nano-containers' exploited.

Monitoring any change in particle shape and morphology. Light scattering detection with different polarizability will be customized to allow particle dimensions to be measured for particles with different shapes.

Technical Specifications

A complete multi-stage front-end that extracts, dilutes, and conditions sample from reactors and other vessels (i.e. also for equilibrium systems) to produce a continuous stream of highly dilute, conditioned sample for detection. This versatile front-end will allow extraction from low viscosity emulsion polymerization fluids up to pure bulk polymerization reactions where the viscosity can approach $10^6$ cP. Conditioning steps will include filtration, debubbling, volatilizing monomers, inverting phase, etc.

There is also provision for interrupted sampling and auto-injection, whereas the system can be modularly switched into use as a comprehensive multi-detector chromatography system. Solenoid or other valves can be provided on those detectors that are flow or shear sensitive to provide a stop-flow capability that does not interfere in any way with the continuously flowing stream. In this mode, the continuous stream is periodically switched into the flow sensitive detector's sample cell by a diverter valve, stopped, and a measurement is made on the stationary solution. During the stopped time, the sample stream continues to bypass the flow sensitive detector's sample cell. Any time after the measurement the continuous flow can be rediverted through the flow sensitive detector's sample cell, then stopped, and another measurement cycle can be made. This strategy is used for example in the NanoDSL (a dynamic light scattering instrument by Brookhaven Instruments Corporation).

The detection end is highly modular, and consists of i) a polymer characterizing detector train—multiangle light scattering, refractive index, viscosity, UV absorption—, ii) a particle characterizing train, such as dynamic and Mie light scattering, and iii) a high throughput, multi-detector train, including a new family of SMSLS cells (simultaneous multiples sample light scattering, a Reed patent held by Tulane), adaptation of SMSLS to high throughput fluorescence detection, and a multi-head peristaltic pump approach to monitoring the effects of multiple solvents and interacting molecules on the polymer. Additionally, polarizing optics and a circular dichroism detector allow a range of new capabilities where particle anisotropy is involved. Where the stimuli responsiveness acquired is the ability to undergo chemical reactions with other specific reagents then it will be possible to use thermography, by mounting a thermally sensitive camera that can thermally image all the different channels in the multidetector train. In this way it can be detected whether an exothermic or endothermic chemical reaction is occurring. Where the stimuli responsiveness changes the color or visual aspect of the polymer and/or colloid, or the color of any complexes or associations that these may form with other agents, then an optical camera can be used to directly visualize and capture the different channels in the multidetector train.

A versatile platform of pumps and detectors is preferred to allow customized methods to be applied in the study of various processes. Components of the apparatus of the present invention and preparation of the apparatus for use can include the following:

Two Q-pumps (Fluid metering);
Five Shimadzu HPLC pumps;
Shimadzu quaternary mixer;
One Zenith gear pump;
Micro-flow controller w/feedback capability;
Mixing chambers/plumbing;
National Instruments comprehensive data interface;
Hardware and GUI integration software;
Software development;
Two multi-head peristaltic pumps;
Machining of SMSLS cells;
Nano-DLS (BIC), dynamic light scattering;
BI-MwA (BIC) 7 angle multi-angle light scattering;
Shimadzu UV/visible diode array flow capable;
Shimadzu refractometer;
Technical support for construction of instrumentation;
Polarization components/analyzers/optoelectronics;
GPC columns, autoinjector; and
Circular dichroism flow ready detector.
Thermal imaging camera
Optical imaging camera The evolution of the properties of the polymers and/or colloids during synthesis can be monitored, for example, according to any of the methods of U.S. Pat. No. 6,653,150.

As used herein, a 'reactive medium' (sometimes referred to as reactor fluid), includes all reagents (such as monomers, initiators, catalysts, surfactants, natural and/or synthetic polymers, etc.), and any other supporting components or fluids (such as solvent or mixtures of solvents in which the reagents are dissolved or suspended, and components which control the characteristics of the reactive medium, such as temperature, pressure, viscosity, color, ionic strength, pH, concentration of the reagents, etc.). Note that not all of the components or fluids in the reactive medium are reagents; i.e. some just control characteristics of the reactive medium (e.g pH, ionic strength, viscosity) without themselves reacting.

The reactor is preferably 'sampled' continuously, or if not continuously substantially continuously. Detector measurements might better be termed 'detector measurement rates' rather than 'sampling rates', and they could also be called 'detector readings'. Typically when a detector measurement is made, it means that at that time the signals from the multiplicity of detectors are captured and stored by the computer. E.g. every second one might measure the signals from all the detectors and store them. This act of measurement might include hundreds or even thousands of data points; e.g. 600 data points from a UV/visible detector, seven or more angles from light scattering, two or more signals from viscosity, multiple thermocouple (temperature) readings, etc.

Preferably, the material from the reactor is drawn continuously or substantially continuously, and readings are taken continuously or substantially continuously. Whether the withdrawals from the reactor are continuous or substantially continuous, the detector measurements are preferably taken at a frequency adequate to provide useful information about the process to allow the process to be advantageously modified to optimize desired results. Detector measurement intervals can be anywhere from every 0.01 s to hundreds of seconds to thousands of seconds, depending on how fast the reaction is. Typically one would set up the detector measurement interval so that there will be roughly ten thousand time points at which the ensemble of detector readings are made during the course of the experiment. E.g. for a three hour reaction one would likely record measurements from all the detector signals every second and get about 10,000 total detector measurement points. It is also frequently the case that different detector signals are measured at different rates. For example, when interrupted chromatographic (GPC) detection is used, there will necessarily be a delay of at least several minutes between detector measurement due to the separation process, so that there will normally be only a few GPC measurement per hour (e.g. 6), and there will not be thousands of measurements.

The present invention can potentially provide continuous phase diagrams, which could be of immense value. As examples, one could determine, with the multi-head peristaltic approach and the temperature controlled SMSLS cells, an LCST phase diagram for a polymer during synthesis, which would demarcate the LCST transition as a function of both temperature and ionic strength. This is a major advance, because such phase diagrams take considerable time to determine individually using standard methods, and the possibility of having virtually a continuous set of phase diagrams at each point of a polymer's and/or colloid's synthetic evolution will be of critical importance in developing new polymers and/or colloids and formulations involving these. Other examples of determining phase diagrams at each moment of evolution can include how a given polymer and/or colloid at each instant of its synthesis interacts with different types and/or concentrations of surfactants, salts, and other agents.

Typical temperatures during polymer and/or colloid synthesis range from −20 C to 300 C, but are more usually in the range of 20 C to 180 C.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 11 shows $M_w$ vs. conversion, f: from uncontrolled free radical to controlled radical behavior (RAFT polymerization of butyl acrylate);

FIG. 12 shows simultaneous monitoring with ACOMP of particle and polymer/monomer features: emulsion polymerization of methyl methacrylate;

DETAILED DESCRIPTION OF THE INVENTION

Figure 1:
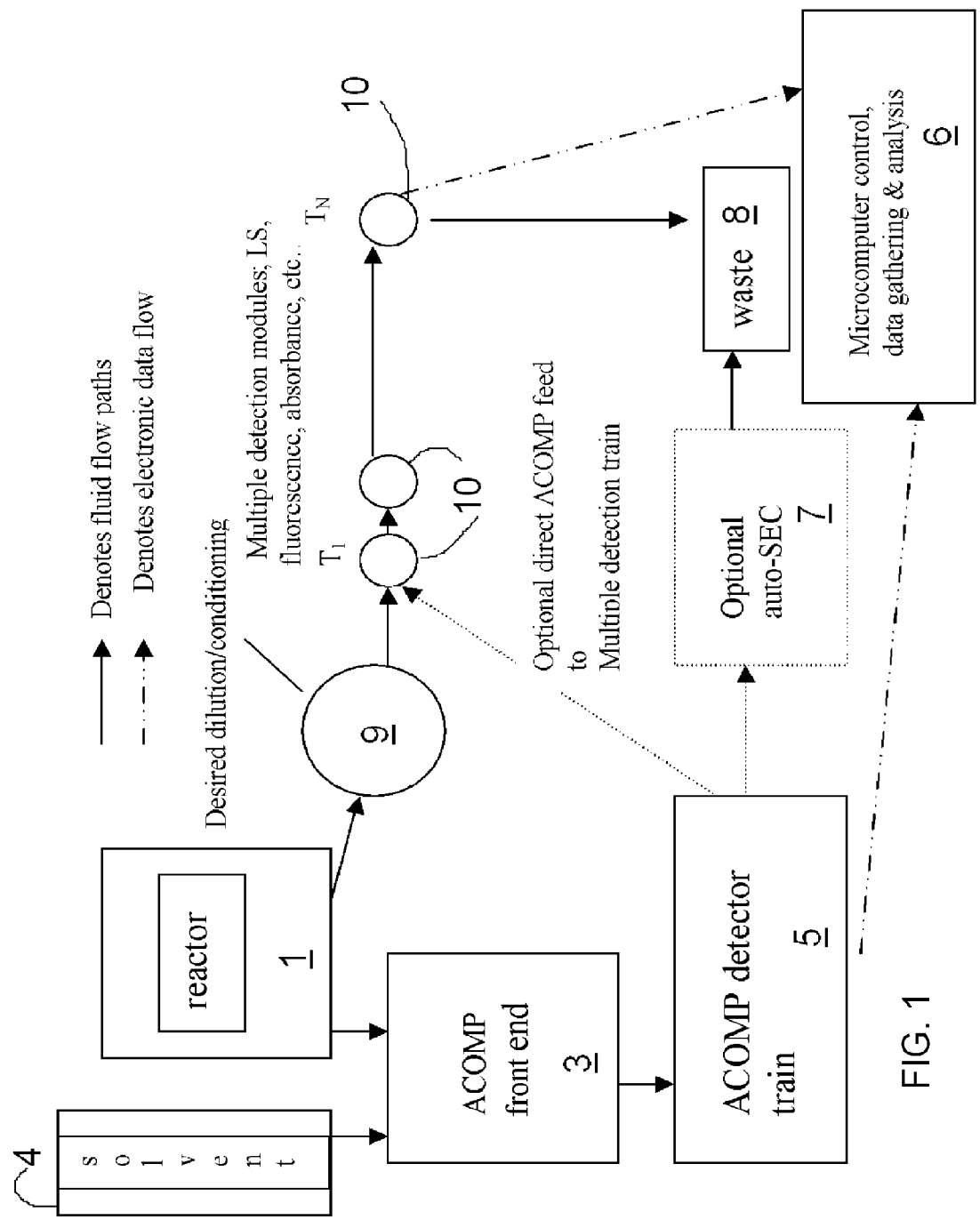
FIG. 1 is a schematic flow chart of a preferred embodiment of the apparatus of the present invention.

Herein, 'evolution of stimuli responsiveness' refers to how the ability of polymers and/or colloids to go through phase and conformational transitions, associations with other molecules, synthetic and biomacromolecules, supramolecular and self-organizing assemblage, reactivities with other species, etc., as defined above, changes as the properties of the polymers and/or colloids themselves change during synthesis; i.e. how changing properties such as molecular mass, composition, comonomer sequentiality (e.g. block, gradient, random), grafting, cross-linking, microgelation, bioconjugation, association with nanoparticles, whether covalent or non-covalent, and post-polymer chemical and physical modifications (such modifications can include, but are not limited to quaternization, PEGylation, sulfonation, carboxylation, amination, 'clicking' on of any one or combination of functional groups or oligomers or polymers) etc. affect these types of stimuli responsiveness, and how the polymer medium—its temperature, pH, ionic strength, solvent type, including use of ionic liquids and including mixtures of solvents, content of surfactants, small molecules, including drugs and other bioactive agents, irradiation by light or other electromagnetic radiation, ultrasound, etc.—affect stimuli responsiveness.

The types of reactions that can produce polymers and colloids with stimuli responsiveness include, but are not limited to free radical polymerization, polycondensation and other step-growth reactions, 'living' type polymerizations, including Ring Opening Metathesis Polymerization (ROMP), Nitroxide Mediated Polymerization (NMP), Atom Transfer Radical Polymerization (ATRP), Reversible Addition Fragmentation chain Transfer (RAFT), anionic and cationic polymerization, post-polymerization reactions that add, subtract, or modify specific chemical groups or moities, etc. The invention can be applied to many different scenarios for polymerization; in solvent, in bulk, in heterogeneous phase, such as emulsion, suspension, miniemulsion, micelle, and inverse emulsion.

Moreover, the invention can be used for different approaches to carrying out the polymerization process; batch reactions in which all reagents are added to the reactor at once, or in discrete amounts as the reaction proceeds, 'semi-batch' reactions, in which the reagents are added to the reactor continuously over intervals or throughout the reaction with constant or changing flow rates for one or more reagents, and continuous reactors, in which reactants are continuously fed together, react together, and are retrieved continuously from the reactor. The latter include, but are not limited to tubular reactors, plug flow reactors, and continuously stirred tank reactors.

In the case of semi-batch and continuous reactors it will be possible to make predictive control of the reactions, that is, by understanding the kinetics of the reaction, such as composition and molecular weight drift, and by understanding how these characteristics produce the desired stimuli responsiveness of the polymers produced, it will be possible to produce the desired polymers 'on-command', by being able to predictively set the reaction conditions to achieve this; e.g. by setting the temperature and concentration of reagents, and by semi-batch flow addition of reagents to control the reaction pathway. Recently the inventor has demonstrated how this predictive approach can be used to control kinetics, molecular weight and composition drift during free radical homopolymerization and copolymerization.

Ultimately, it will also be possible to use full feedback control of reaction conditions, such as reagent flows into the reactors to produce polymers with desired stimuli responsiveness. In this scenario the sensing of the polymer characteristics (conversion, molecular weight, etc.) and/or the sensing of the stimuli responsiveness can be used to automatically adjust reaction conditions (e.g. temperature) and reagent flow conditions to control the reaction towards the desired product.

Best current approaches to assaying stimuli responsiveness involve high throughput screening of end-products, such as multiple well, channel plates, or even continuous gradient devices (e.g. Bergbreiter et al., Macromolecules, 37, 2004, 1031-1036) on which detection of transitions can be made with any appropriate spectroscopic or other method. These, however, test only the endproduct, and so have no means of determining when during synthesis the particular phase transition properties of the polymer appeared or began to appear. It would take many more polymerization reactions to explore even a finite number of compositions and molecular weights, etc., whereas the proposed during-synthesis method allows one to continuously, and in a single experiment, make precise determinations of the polymer characteristics required for sharp or gradual threshold behavior.

The idea of during-synthesis monitoring presented here is that the evolution of stimuli responsiveness can be monitored versus continuously changing molecular weight, composition, and other molecular features (e.g. polyelectrolyte linear charge density, polymer branching, cross-linking, 'clicking' to other molecules and polymers, etc.) as the polymers evolve during their synthesis. This sets the method totally apart from all traditional methods and even the most modern high-throughput methods that analyze only endproducts of multiple reactions carried out in parallel, which hence only measure discrete variations in polymer parameters. In other words, the present invention allows stimuli responsiveness to be assessed on the equivalent of a complete continuum of endproducts, rather than a mere sampling of individually synthesized endproducts. The invention, even in its simplest form, is a high throughput screening platform.

In fact, if carried out vigorously and successfully, this approach could directly challenge and perhaps even disrupt the currently growing area of multiple, simultaneous, robotically controlled reactions, whose endproducts are analyzed (Wiesbrock, F.; Schubert, U. S. "New challenges in combinatorial polymer research: 3rd DPI workshop on automated synthesis and high-throughput experimentation in polymer and materials research at the Eindhoven University of Technology." Macromolecular Rapid Communications (2004), 25(17), 1579-1582); e.g. Symyx Corporation, Chemspeed AG. For example, those very expensive technologies (which easily run into the million dollar range and more per system), are often used to produce merely a series of polymer end products of the same composition but different molecular weight in order to assess the dependence of stimuli responsiveness on this latter property. They may also be used to produce a variety of endproducts of different compositions, masses, and other properties, but they are still limited to endproduct analysis.

The present invention is quite elegant as it both provides the equivalent of a continuum of endproducts while vastly reducing the number of reactions to be run. This idea is particularly well-suited to many 'living' types of polymer reactions; e.g. controlled radical polymerization reactions such as nitroxide mediated polymerization (NMP); reversible addition fragmentation chain transfer (RAFT); atom transfer radical polymerization (ATRP); and other 'living' type reactions, such as ring opening metathesis polymerization (ROMP), where growing chains usually share similar mass and composition averages. The invention will also be applicable to post-polymerization modifications (hydrolysis, PEGylation, 'click' coupling, etc.), step growth, free radical chain growth, grafting, branching, bioconjugation, etc. It is suited to many types of reaction scenarios, including batch reactors, 'semi-batch' reactors, that is, controlled feed of one or more reagents affecting polymerization into the reactor during the reaction, and continuous reactors.

A major advantage of the proposed method is that it can provide a fast track towards optimization of polymer properties required to carry out desired functions, such as sensing, encapsulation, coating, etc. by precisely quantifying how stimuli responsiveness evolves. Once it is known when during synthesis a polymer achieves desired stimuli responsiveness, and under what types of reaction conditions, polymers of precisely those characteristics at that point of synthesis can then be targeted as end products in subsequent experiments, scale-up operations, or manufacturing.

While many methods exist for observing polymeric phase transitions and/or stimuli responsiveness, e.g. turbidity, fluorescence, conductivity, surface tension, light scattering, circular dichroism and birefringence, including high throughput measurements on reaction endproducts, etc., the present inventor believes that few, if any, during-synthesis methods exist, which simultaneously measure polymer properties, such as mass and composition, and phase transitions.

One of the several advantages of this approach is that it will allow precise knowledge of at what point in synthesis, polymers and copolymers obtain, whether sharply or gradually, their stimuli responsiveness. For example, an evolving polymer (which henceforth means any type of polymer, whether copolymeric, terpolymeric, etc., gradient, block, grafted, branched, star, dendrimeric, produced through chemical, enzymatic or other modifications, etc.) may have an LCST, for a given solvent type (whether mixed or pure solvent) and polymer composition and molecular weight, or molecular weight distribution. With an appropriate detector in an ACOMP system, the phase transition at the LCST can be automatically detected, and it is then known what the threshold mass and composition characteristics of the polymer are for the phase transition to occur.

'High Throughput Squared'; Coupling ACOMP to SMSLS and its Successors.

In fact, one can couple extra detectors to the system to make multiple determinations and hence convert the approach to a sort of 'high throughput squared' platform. An example of this would be the use of SMSLS (Simultaneous Multiple Static Light Scattering, patented by W. F. Reed) (W. F. Reed U.S. Pat. No. 6,618,144, "Device and method of simultaneously measuring the light scattering from multiple liquid samples containing polymers and/or colloids"; M. F. Drenski, W. F. Reed, "Simultaneous Multiple Sample Light Scattering for Characterization of Polymer Solutions", J. App. Polym. Sci., vol. 92, 2724-2732, 2004), flow sample cells held at different temperatures in the detector train. In this particular example, one could determine the LCST for as many molecular masses and compositions of polymer as there are SMSLS flow cells at different temperatures. These latter are relatively easy and inexpensive to fabricate, and current data collection systems can handle large numbers. SMSLS flow cells can be modified to measure absorbance and turbidity (as opposed to scattering or fluorescence) if the detection fiber is mounted at an angle of 0° for detection.

With the advent of flow-cell equipped dynamic light scattering (DLS)—e.g. the NanoDLS by Brookhaven Instruments Corporation (Holtsville, N.Y.), single mode detection fibers, and inexpensive autocorrelators, it is possible to create a train of SMSLS type cells for DLS to make measurements of hydrodynamic diameter.

It is noted that where detected properties may be sensitive to flow, e.g. optical measurements of anisotropic particles in shear flow, each detection cell can be equipped with a stop-flow means, whereby a solenoid valve or other automatically switchable element can periodically divert the continuous flow stream into the cell, where it remains stationary during measurement, the continuous flow bypassing it during this interval, and the cell contents being subsequently swept out as the flow again diverts through it until the flow is again diverted from the cell and a new measurement cycle is made on the stopped flow cell contents.

Extending the SMSLS Platform to Fluorescence Detection (a New Instrumentation Family).

The SMSLS cells can be adapted to become multiple fluorescence detecting flow cells; e.g. for a right angle SMSLS cell, one could add an optical notch filter at the photodetector (e.g. CCD) to exclude scattered light and detect only fluorescence. Newport Corporation (Irvine, Calif.), for example, offers a wide variety of narrow bandpass optical filters (e.g. 10BPF10-330). One could also use two right angle fibers (e.g. one on each side of the cell, or both on the same side) each with its own notch or cut-off optical filter for detecting ratios of fluorescence intensities at different wavelengths, as is frequently done with fluorescent probes, for example with pyrene (Narrainen, Amilcar Pillay; Pascual, Sagrario; Haddleton, David M. "Amphiphilic diblock, triblock, and star block copolymers by living radical polymerization: synthesis and aggregation behavior." Journal of Polymer Science, Part A: Polymer Chemistry (2002), 40(4), 439-450.). While incident light is usually provided by lasers in SMSLS flow cell banks, broad band ultraviolet and visible light sources (e.g. xenon and deuterium lamps) could be used where broader ranges of UV/visible excitation than afforded by monochromatic lasers are needed. In such cases filters or monochromators for excitation wavelength selection can be used.

Addition of Polarization Sensitive Detection to the Entire SMSLS Family of Instruments.

As concerns further optical variations of the SMSLS detection platform, additional power for functional evolution can be gained by using polarizing properties. Polarization preserving fibers and inline fiber optical polarizers are readily available to allow sensing of the various states of linear or elliptical polarization of scattered or emitted light. For example Newport Corporation has a whole series of inline fiber optical polarizers available; e.g. F-ILP-1-N-SP-FP. Areas in which polarization sensitive monitoring can be useful include, but are not limited to, formation of anisotropic structures—e.g. self-assembly of rod-like micelles—that lead to depolarized scattering, and inhibited rotations of symmetric or asymmetric probe-containing structures leading to fluorescence emission anisotropy, (Tusa, S. T; Sakakibara, a.; Yamammoto, T.; Morishima, Y. "Fluorescence Studies of pH-responsive unimolecular micelles formed from amphiphilic polysulfonates possessing long chain alkyl carboxyl pendants", Macromolecules (2002), 35, 10182-10288) etc.

Other Aspects of the High Throughput Capabilities.

Similarly, in this single example, one can conceive of many other ways of making simultaneous determinations during synthesis. For example, one reactor stream may feed a typical ACOMP detection train for determining all the relevant polymer parameters as they evolve (composition, mass, conversion, linear charge density, etc.), whereas a separate stream(s) could be drawn and then independently diluted with a series of different diluents, e.g. with a multiple-channel peristaltic pump, the stream for each of which would flow through one or more SMSLS cells. Such multiple-channel pumps are widely available; e.g. the Rainin 7103-058 RP-1 8-channel peristaltic pump. Again, since SMSLS cells are inexpensive and large numbers can be brought under the control of a single computer, each mixed solvent stream could also have a series of SMSLS cells at different temperatures so that now, polymer characteristics for LCST thresholds could additionally be determined as a function of solvent mixture. When the threshold phenomenon is dependent on the concentration of polymer in solution, this same dual or multiple extraction stream could be also used to vary polymer concentration in multiple sub-streams for determination of such concentration dependent effects on LCST and other types of stimuli responsiveness.

There are no limits to the types of multiple diluents that could be assayed simultaneously. They could be different solvents, mixtures of solvents, solutions of different pH, ionic strength, concentrations of metal ions, uni- or multivalent ions, solutions containing aromatic molecules, drugs or their analogs, other synthetic or natural polymers, micelles, vesicles, emulsions, or liposomes that may interact with the evolving polymer, etc.

Besides light scattering, absorbance, and fluorescence detection, it is possible to use optical rotary dispersion and circular dichroism (e.g. useful for detecting helix to coil transitions, denaturation, etc.), conductance, etc., in short, any of the usual means of observing polymer transitions, associations, etc.

There are many examples that can be given besides LCST. For example, copolymers can micellize or form other types of uni- or multi-chain aggregates, depending also on their composition, molecular mass, etc. Use of a fluorescent dye in the ACOMP dilution stream, for example, could give precise information on when micellization occurs, giving a fast track to polymer optimization.

Another example is encapsulation. The desired agent, or an analog of the desired agent, could be put either in the ACOMP dilution stream, and/or in the reactor, and its encapsulation monitored by fluorescence or other method. In this way, one would know under precisely what polymer properties encapsulation occurs. In the same experiment one could also use the multiple stream approach and hence test for the effects of solvent polarity (e.g. through mixtures), pH, ionic strength, different types of agents to be encapsulated (e.g. a series of agents), etc. Yet another example is the use of agents, such as multivalent or metal ions, to produce supramolecular (non-covalent) associations between polymers.

Other Aspects of the Relationship to ACOMP and SMSLS.

An interesting feature of this approach is that it builds off of instrumentation and methods platforms already patented by Reed and held by Tulane. To utilize the present invention as outlined here, at least, would preferably involve use of the patented ACOMP platform. To use the multiple temperature on a single stream, or in the multiple stream approach would preferably involve use of patented SMSLS instrumentation.

The SMSLS instrumentation, as noted above, can be modified to become Simultaneous Multiple Sample Fluorescence Detection, Simultaneous Multiple Sample Absorption Detection, etc. These cells can also be fitted with light sources to form other functions besides detection; e.g. photodecomposition, photoactivation, photoassociation, photoacidification, etc. That is, instead of irradiating the cells with electromagnetic radiation used solely as a probe, such as for scattering or fluorescence, the incident radiation could actually excite functional properties of the polymers, such as photoacidification where a proton is photostimulated to leave its parent molecule. In general the invention can monitor radiation sensitivity of the polymers, whether the radiation be electromagnetic, such as visible light, ultraviolet, x-rays, etc., or charged particles, such as electrons. Each sample cell could be constructed to each have a different intensity or type of radiation (e.g. different wavelengths or colors of light) incident on it, for example, through windows that are in contact with the flow channels.

In fact, the present invention can be viewed as a 'next generation' ACOMP system in that it benefits from the information (molecular mass, conversion, composition, etc.) provided by the 'first generation' ACOMP and uses this information to correlate detection of phase transitions and associations therewith. It is also next generation in the sense that it moves into the important realm of mapping out the functional behavior of the explosively growing number of 'intelligent' polymers that will be at the heart of major materials science innovations in the 21st century.

Extension to Natural Products.

The principles outlined above can be readily adapted to the vast area of natural product modification and use. Natural products are frequently modified by chemical, enzymatic, or photomodifications in order to achieve properties such as solubility, biocompatibility, micellization, nanostructuration, etc. This same type of approach could be used as a high throughput platform for monitoring how these properties of natural products evolve as they are extracted, modified, and processed.

Extension to Control of Polymerization Reactions

ACOMP has matured to the point where reactions can be controlled predictively (i.e. using precise reaction kinetics and characteristics furnished by ACOMP to predict optimal reaction processes) and, eventually, by feedback. In those scenarios, the monitoring is used to guide the production of desired molecular weight and composition distributions, degrees of grafting, etc.

FIG. 1 shows a scheme for multiple temperature monitoring of phase transition and association phenomena. The multiple detectors can be of the light scattering, fluorescence, and absorbance types, among others, including any combination that can be used in the train. A separate extraction/dilution/conditioning stage is shown here with the solid arrow. A simpler version uses the ACOMP stream directly (dotted line) so that the multiple transition/association monitoring detectors are simply in series with the rest of the ACOMP detectors.

Figure 2:
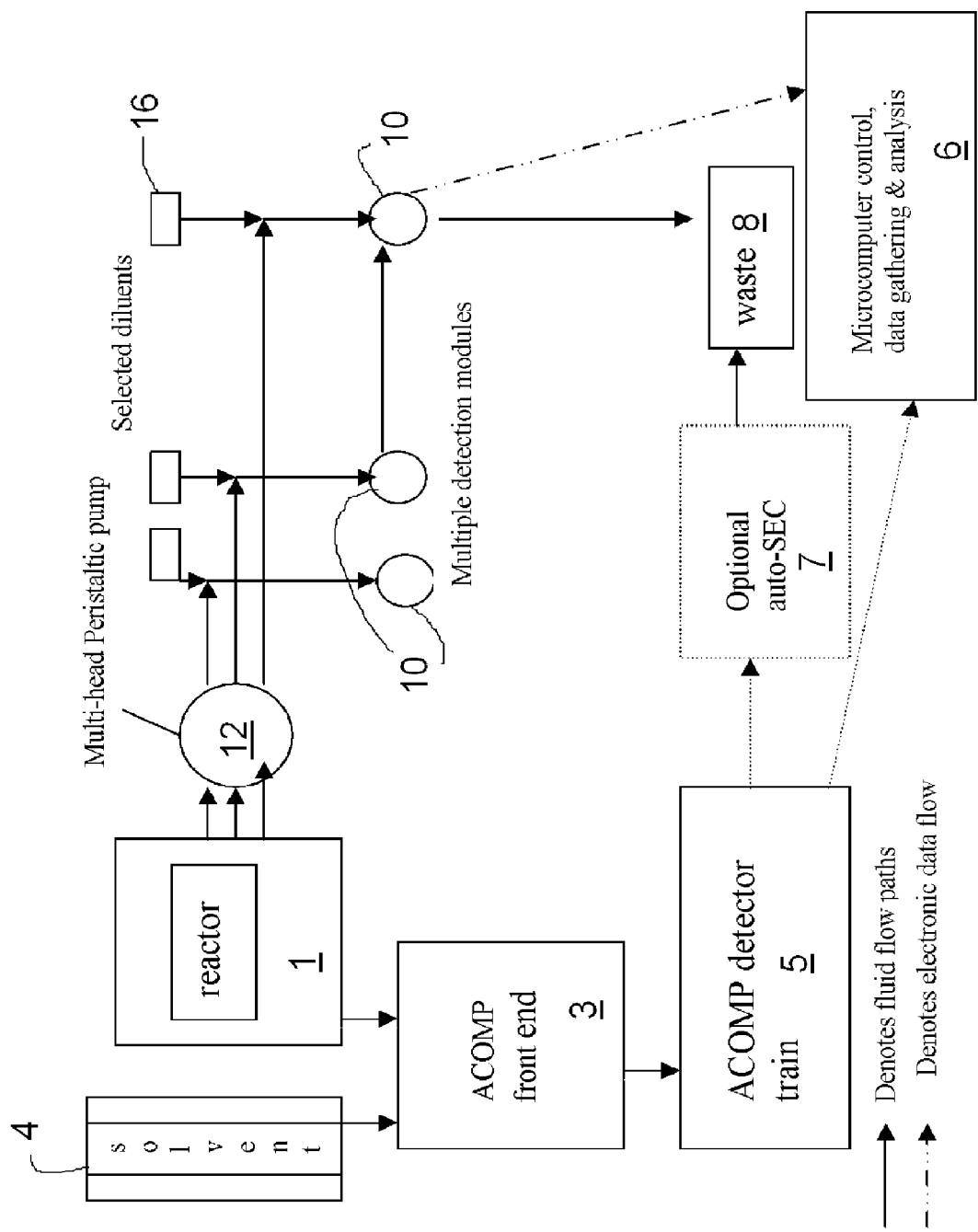
FIG. 2 is an alternate preferred embodiment of the apparatus of the present invention.

FIG. 2 shows a scheme for multiple composition monitoring of phase transition and association phenomena. A multi-head peristaltic pump, or other device(s), can be used to withdraw multiple small sample streams for separate and simultaneous dilution with 'selected diluents'. These latter can be an assortment of any factors desired; e.g. mixed solvents, different solvents, different pH, ionic strength, metal ions, uni- or multivalent ions, diluents containing specific molecules for binding or 'recognition' of the polymer, enzymes, polypeptides, etc. The multiple detectors can be of the light scattering, fluorescence, and absorbance types, among others, such as capillary viscometers, including any combination that can be used in the train.

Figure 3:
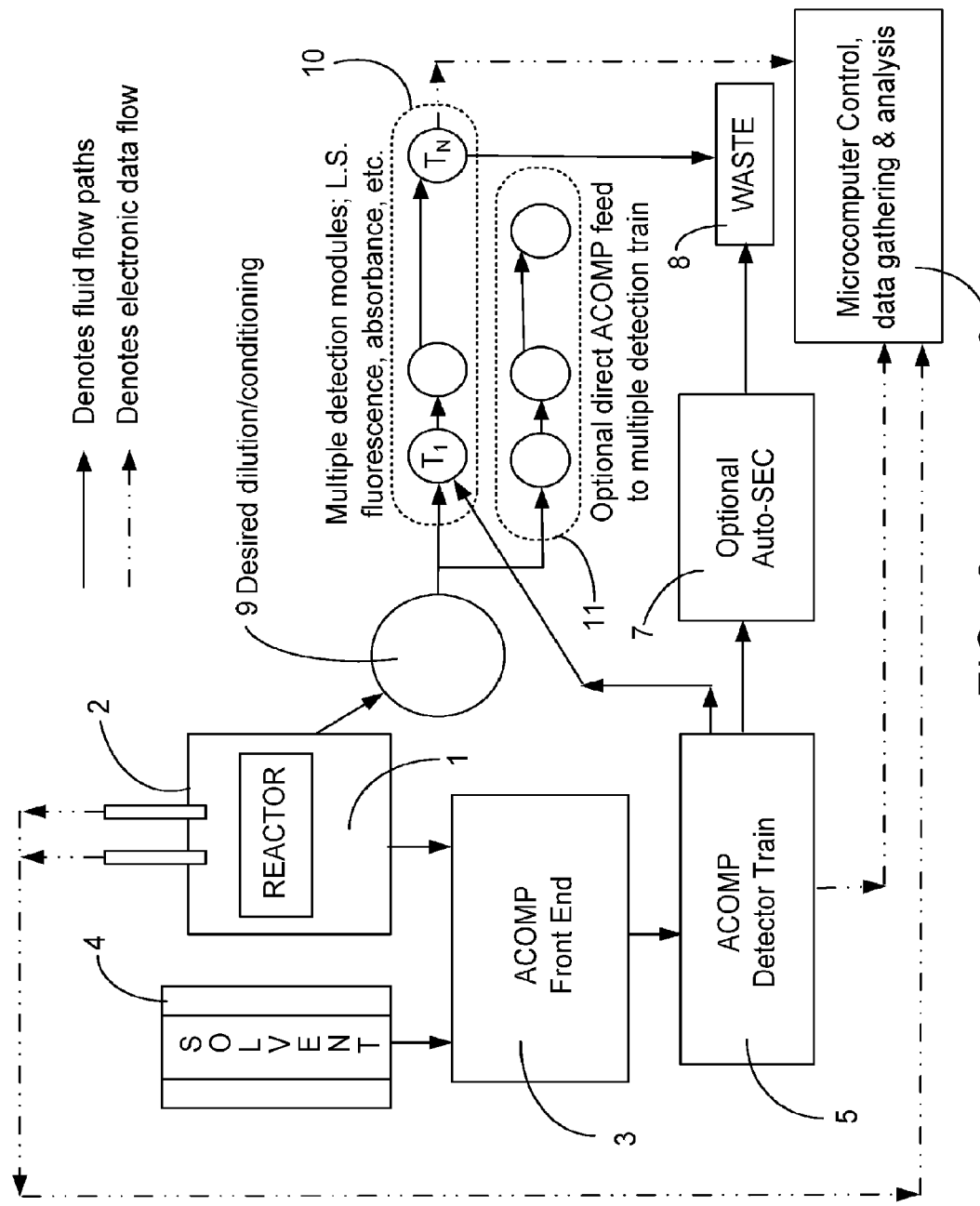
FIG. 3 is schematic flow chart of an alternative embodiment of the apparatus of the present invention.

Shown in FIG. 3 is a polymerization reactor 1, which is preferably controllable, thermostatted temperature, with mechanical stirring, inlet/outlet access ports, and optional condenser (e.g. Ace Glass). There can be optional reactor probes 2, such as pH and/or conductivity sensors, and/or near infrared and/or mid-infrared probes, and/or Raman probe. The ACOMP front end 3 comprises one or more of the following components (see Polymer International, 57, 390-396, 2008)—this list is not necessarily exhaustive:

a pump for extraction from the reactor, e.g. Zenith Corp. gear pump;

an optional recirculation loop from the reactor through the extraction pump and back into the reactor;

an optional pressure transducer in the recirculation loop that measures reactor content viscosity;

an optional mass flow controller that provides a controllable steady pick-off from the recirculation loop into the low pressure mixing chamber (LPMC), e.g. Bronkhorst;

an LPMC, such as a stirred, thermostatted vial with inlet and outlet connections for fluid entrance and egress; reactor fluid is diluted to any desired level in the LPMC, and it is preferably vented to the atmosphere to allow release of any gas bubbles generated in the reactor;

an LPMC level control, such as an auxiliary pump with extraction tube at fixed height within the LPMC;

an optional high pressure mixing stage and pump or LPMC and pump to achieve higher levels of dilution, if desired;

acapillary tube leading to the detector train.

The solvent reservoir 4 can be a vessel (four-liter capacity, for example) containing dilution solvent or solvent mixture of choice, with tubes in the vessel for extraction by the various pumps for diluting and mixing the sample flow, and feeding the detector train. The ACOMP detector train 5 preferably comprises one or more of the following instruments:

- multi-angle static light scattering detector, e.g. Brookhaven Instruments Corp. BI-MwA;
- dynamic light scattering detector, e.g. Brookhaven Instruments Corp. nano-DLS;
- Mie light scattering detector, e.g. Malvern Mastersizer;
- single or multiple capillary viscometer, e.g. using Validyne pressure transducers;
- ultraviolet/visible spectrophotometer, e.g. Shimadzu Diode Array SPD-M20A;
- differential refractometer, e.g. Shimadzu RID-10A;
- near infra red or mid-infra red detector, e.g. Shimadzu.

The microcomputer control 6, for data gathering and analysis, can comprise:

- an integrated instrument control device and signal processor for detector train signals, e.g. the National Instruments NI Compact Field Point Model CFP-2020 Part #: 188539G-03;
- a software program(s) allowing control of the instruments and graphical display of the incoming and analyzed data, e.g. Labview software modules;
- software for numerical data analysis of signals; e.g. written in C++ or other programming language (Power Basic, Visual Basic, Fortran), and embedded into control program, or running simultaneously with it;
- a computer for running the control, data gathering and analysis software, e.g. any standard desktop or laptop computer, such as from Gateway, Hewlett Packard, Apple or Dell.

The optional auto-SEC (Size Exclusion Chromatography) 7 is connected to the waste stream from the ACOMP detector train 5, or directly to the outlet stream of the ACOMP front end 3 if no continuous detector train 5 is used. The auto-SEC 7 can be equipped with:

- an auto-injector valve connected to the stream as mentioned, and set to automatically make injections of small volumes (e.g. 100 microliters) into the SEC columns at desired intervals (e.g. every 10 minutes);
- a high pressure liquid chromatography pump; e.g. Shimadzu LC10-AD;
- a solvent reservoir, which can be the same as solvent reservoir 4 if desired and appropriate;
- one or more SEC columns;
- a software program for gathering and analyzing the data from the periodically injected samples;
- any combination of the following detectors: multi-angle static light scattering detector, e.g. Brookhaven Instruments Corp. BI-MwA; dynamic light scattering detector, e.g. Brookhaven Instruments Corp. nano-DLS; Mie light scattering detector, e.g. Malvern Mastersizer; single or multiple capillary viscometer, e.g. using Validyne pressure transducers; ultraviolet/visible spectrophotometer, e.g. Shimadzu Diode Array; differential refractometer, e.g. Shimadzu; near infra red or mid-infra red detector, e.g. Shimadzu.

Waste vessel 8 is preferably provided to accumulate the waste streams of solvent and sample produced by the system and can be e.g. a safety sealed metal drum. Desired dilution/conditioning 9 can have the same function as ACOMP front-end 3. In some applications it can be ACOMP front-end 3 itself, in other applications it can contain those elements of ACOMP front-end 3 necessary to provide the dilution/conditioning needed to monitor stimuli responsiveness of the polymers. Multiple detection modules 10 are preferably independently controlled, and monitored, e.g. for temperature, illumination, and can include multiple individual capillary viscometers, static light scattering cells (e.g. SMSLS—see (U.S. Pat. No. 6,618,144)), dynamic light scattering, fluorescence, and turbidity cells. Optional multiple detection modules 11 in parallel with modules 10, including a valve or 'T' for splitting the flow between modules 10 and modules 11. These can be used to incorporate more banks of individually controlled and monitored detectors.

Living Diblock

Figure 4:
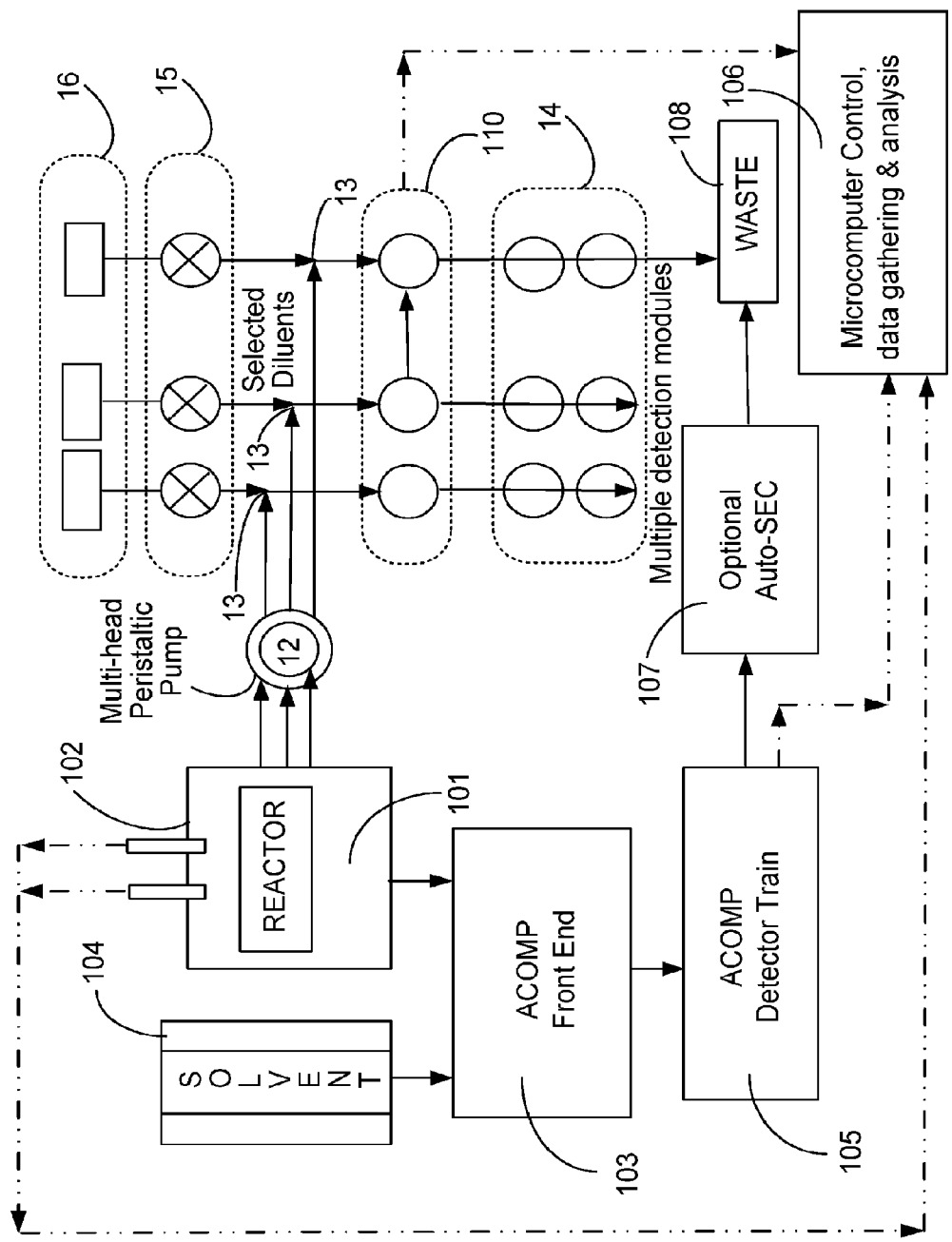
FIG. 4 is a specific embodiment for using the invention to characterize the salt sensitivity of micellization, polymer dimensions, and interactions during the synthesis of a copolymeric polyelectrolyte, of the block, random, or gradient type—this is just an example of numerous applications of the invention.
Figure 5:
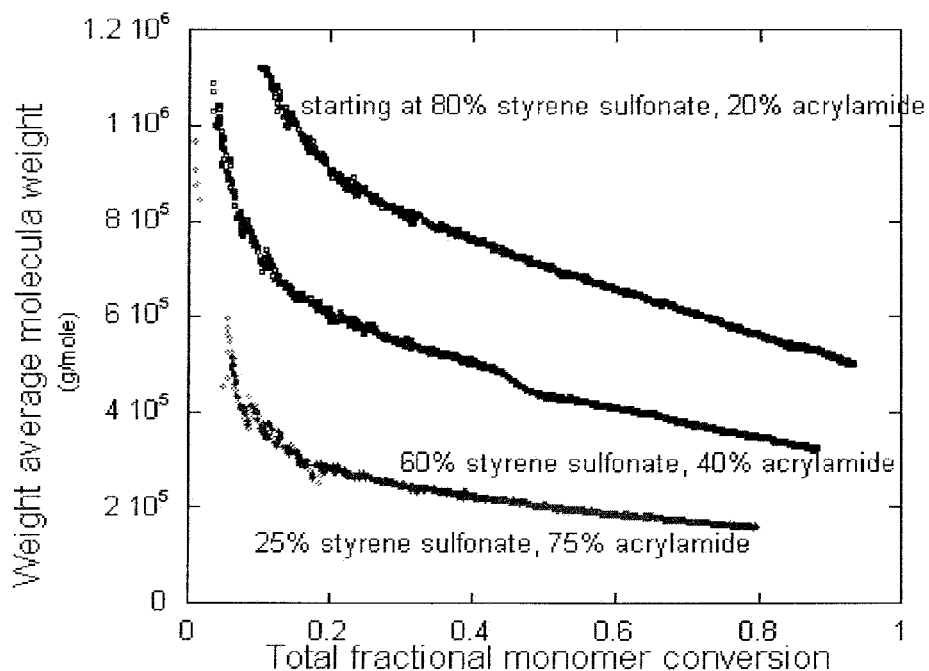
FIG. 5 shows examples of weight average molecular weight for a polyelectrolyte free radical copolymerization using styrene sulfonate and acrylamide (Adapted from T. Kreft and W. Reed, Publication Date (Web): May 22, 2009 (Letter) DOI: 10.1021/jp903520s, J. Phys. Chem B, web edition, hard version in press)
Figure 6:
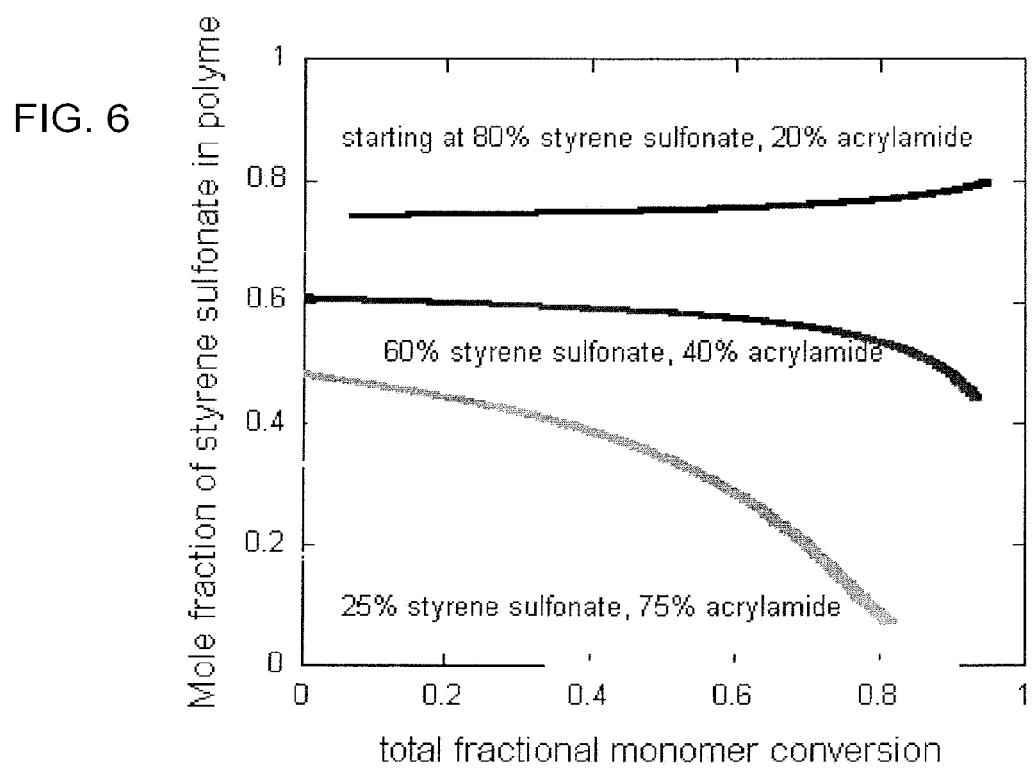
FIG. 6 shows the type of composition drift for these same reactions.
Figure 7:
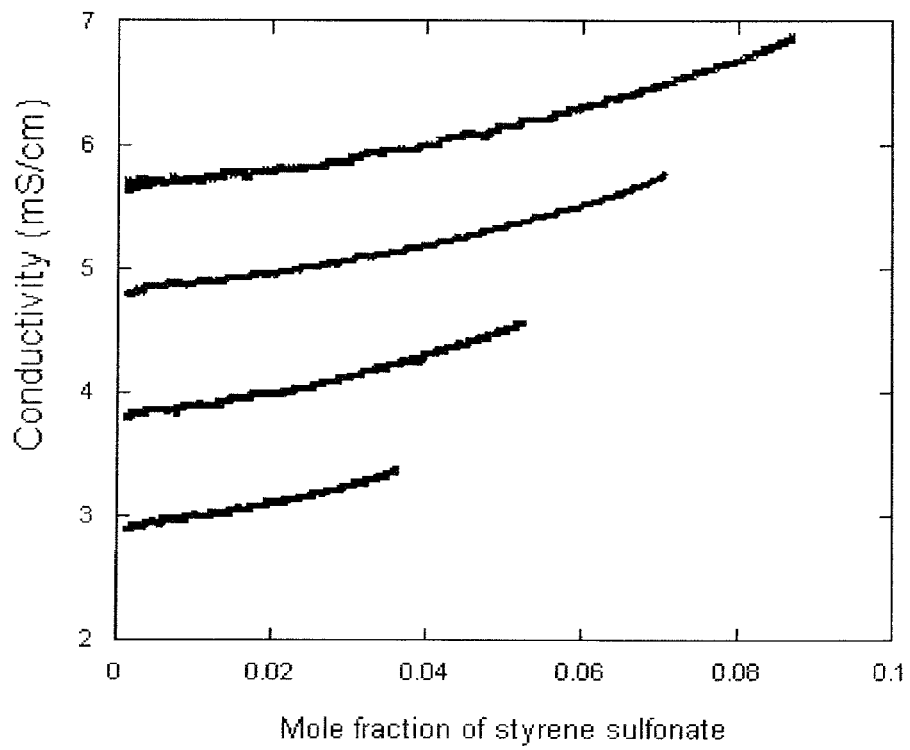
FIG. 7 shows how conductivity changes for several of these reactions.
Figure 8:
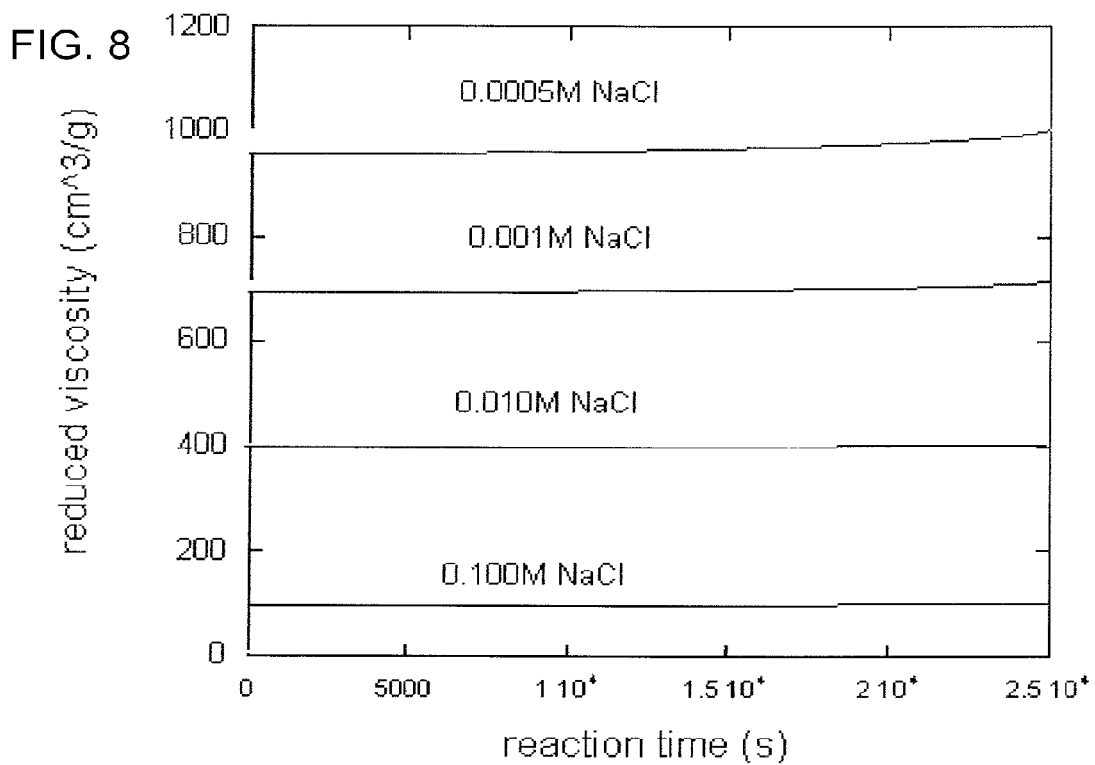
FIG. 8 is an anticipated result for viscosity signals for the experiment starting at 80% styrene sulfonate and 20% acrylamide, for which there is little composition drift.
Figure 9:
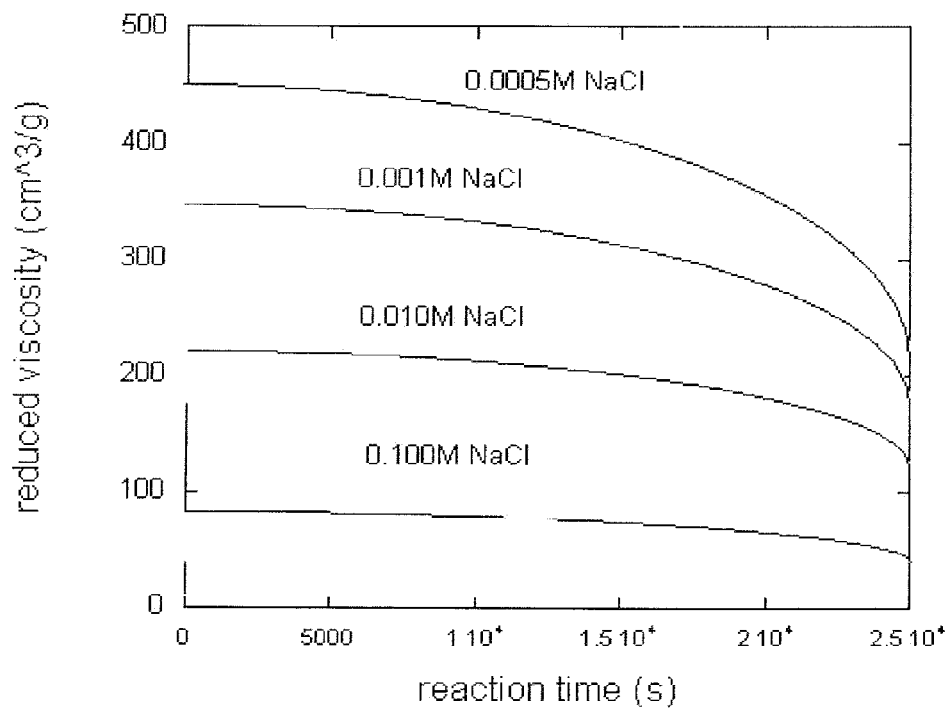
FIG. 9 is a sharp contrast to FIG. 8, showing the type of behavior expected for viscosity signals for the experiment starting at 25% styrene sulfonate and 75% acrylamide, for which there is large composition drift, and the chains produced have decreasing amounts of styrene sulfonate (charged monomer) and so have decreasing viscosities. Since this system is not expected to micellize, there would be no expected change in pyridine fluorescence vs. time for the different ionic strengths.

FIG. 4 is a specific embodiment for using the invention to characterize the salt sensitivity of micellization, polymer dimensions, and interactions during the synthesis of a copolymeric polyelectrolyte, of the block, random, or gradient type—this is just an example of numerous applications of the invention.

Elements 1-8, and 10 in FIG. 3 can the same for FIG. 4. Element 9 from FIG. 3 is replaced by pump 12. Element 11 from FIG. 3 is omitted and replaced by detectors 14. Elements 12, 13, and 14 are described below. For this specific embodiment those elements corresponding to elements 1-10 in FIG. 3 are specified more exactly than in FIG. 3 to avoid too many optional features. The specific items used and their combinations are not construed as limiting. A jacketed polymerization reactor 101, is preferably thermostatted with temperature control from 2° C. to 220° C., using recirculating oil from a thermostatted batch. Reactor 101 preferably has a mechanical stirring paddle, controllable from 10 to 1000 RPM, inlet ports for purging with nitrogen or other gas, introducing reagents either with a syringe or with a pump, a tube for extracting the reactor contents, access ports for sensors 102, and a condenser fitted to the top. Reactor 101 is normally sealed and kept under a blanket of nitrogen at slightly higher than atmospheric pressure. A copolymeric polyelectrolyte synthesis reaction is chosen in this example, and long, electrically charged polymer chains are produced during the reaction. Reactor conductivity sensors 102 can include a Jenway conductivity probe and pH probe, for example. ACOMP front end 103 in this configuration preferably comprises the following components. The list is not necessarily exhaustive:

- a Shimadzu HPLC pump for extraction from the reactor;
- a pressure transducer with a capillary in the outlet flow of the HPLC pump that measures undiluted reactor content viscosity;
- an LPMC, consisting of a thermostatted vial with an inlet tube from the HPLC reactor withdrawal pump that has a perforated outlet orifice to promote viscous liquid dispersal, and an outlet tube for continuous extraction of the diluted LPMC content; reactor fluid is diluted to any desired level in the LPMC, and the LPMC is preferably vented to the atmosphere to allow release of any gas bubbles generated in the reactor;
- an LPMC level control, consisting of an HPLC or peristaltic auxiliary pump with extraction tube at fixed height within the LPMC. This guarantees maintaining the same level and volume in the LPMC throughout the reaction. The outlet of this level controlling pump goes to waste vessel 108;
- a high pressure mixing stage, an Upchurch Corp. 10 microliter high pressure mixing 'T'. One end of the 'T' is fed by the diluted fluid leaving the LPMC using a separate HPLC pump, and another, separate HPLC pump feeds the other end of the 'T', and provides the desired final dilution level and also feed the detector train via a capillary tube leaving the high pressure mixing 'T' chamber.

A solvent reservoir 104 can be a vessel (e.g., a four liter glass container) containing dilution solvent, with tubes in the vessel for extraction by the various pumps for diluting and mixing the sample flow, and feeding the detector train. An ACOMP detector train 105 preferably the following instruments.

- a multi-angle static light scattering detector; e.g. Brookhaven Instruments Corp. BI-MwA. The expansion board on this preferably accepts signals from all the other detectors;
- a dynamic light scattering detector, e.g. Brookhaven Instruments Corp. nano-DLS;
- a Mie light scattering detector, e.g. Malvern Mastersizer;
- a single capillary viscometer, using a Validyne pressure transducer, according to the design of Norwood and Reed (see Int. J. Polym. Ana. and Char., 4, 99-132, 1997);
- a two wavelength ultraviolet/visible spectrophotometer, e.g. Shimadzu Diode Array;
- a differential refractometer, e.g. Shimadzu.

A microcomputer control 106 for data gathering and analysis preferably comprises:

- a Brookhaven Instruments Corp. software program that gathers, via an A/D expansion board on the BI-MwA detector, and graphically displays, the incoming and analyzed data.
- software for numerical data analysis of signals written for example in Power Basic;
- a Dell microcomputer with an Intel Core 2 duo processor and USB connection.

Auto-SEC (Size Exclusion Chromatography) 107 is connected to the waste stream from the ACOMP detector train 105. The auto-SEC 107 is preferably equipped with:

- a Rheodyne MXP 7900 auto-injector valve with a 100 µl sample loop attached; an Amperite solid state DFA series adjustable recycling timer is used to control the valve for periodic injections;
- a Shodex 804 SEC column;
- a Shimadzu high pressure liquid chromatography pump;
- a solvent reservoir, which can be the same as reservoir 104;
- a BI-MwA based program for gathering and analyzing the data from the periodically injected samples;
- the following detectors: a multi-angle static light scattering detector; e.g. Brookhaven Instruments Corp. BI-MwA, a dynamic light scattering detector by Brookhaven Instruments Corp. nano-DLS, i.e. light scattering detector by Malvern Mastersizer, a single capillary viscometer;
- a Shimadzu dual wavelength ultraviolet/visible spectrophotometer;
- a Shimadzu differential refractometer.

A (for example four-liter glass) waste vessel 108 to accumulate the waste streams of solvent and sample produced by the system. There are preferably ten custom fabricated individual static light scattering cells 110 in series, similar to the Simultaneous Multiple Sample Light Scattering patent (U.S. Pat. No. 6,618,144) of Reed. Each cell preferably has 90 degree fiber optic detection of scattered light and its own Pelletier temperature control element. A diode laser (Laser Max) at 635 nm is preferably used, in conjunction with beam splitters, to illuminate the cells. Scattered light detected by each fiber optic is preferably fed to an individual photodiode. These cells are fed by the diluted output from the mixing 'Ts' 13, which 'Ts' 13 are each fed by one capillary from multi-head pump 12 and multi-head pump 15. The multi-head peristaltic pump 12 for dilution/conditioning can comprise for example Masterflex (Cole-Parmer) Model 7523-30. Each capillary tube from the head is preferably immersed in the reactor and draws separate microstreams at preferably about 50 microliters per minute. Mixing 'Ts' 13 accept reactor fluid from pump 12 and dilution fluid from the second multi-head peristaltic pump 15. Two rows 14 of ten detectors each can include a first row of ten detectors preferably comprising ten single capillary viscometers each fed in series by an outlet stream from one of the ten light scattering cells 110. The second row preferably comprises ten custom built fluorescence detection cells, each temperature thermostatted, and each with dual 90 degree fiber optics mounted integrally to the cell, after the fashion of the SMSLS-type cells 110. The cells are preferably illuminated with a laser, and optical notch filters from Newport Corp. detect the fluorescent light. A second peristaltic pump 15, such as pump 12, with each capillary, however, preferably extracting solvents from different dilution reservoirs 16. Dilution reservoirs 16 preferably contain aqueous solvent at different ionic strengths, and preferably with an appropriate pyridine dye or derivative that changes fluorescence properties when the polyelectrolyte micellizes.

Here is a scenario of how the whole system might work: For concreteness we synthesize a random copolymer, with a charged monomer (e.g. styrene sulfonate, a quaternized acrylamide, etc.) and a neutral monomer (e.g. acrylamide, vinyl pyrrolidone, etc.). These are at 2.1% by combined weight in an aqueous reactor solution containing 0.005M of NaCl, with a total volume of 750 ml. A suitable free radical initiator is used (e.g. potassium persulfate) to initiate the reaction, carried out in the reactor 101 under $N_2$ at 60 degrees C. The conductivity and pH probes monitor these characteristics within the reactor throughout the reaction. (In a second experiment we synthesize a diblock copolymer using controlled radical polymerization.)

The front-end 103 extracts reactor liquid at the rate of 0.05 mL/minute which is led to the LPMC and mixed with 0.1M NaCl aqueous solvent from reservoir 104 entering the LPMC at 1.0 mL/min, yielding a 21 fold dilution. LPMC liquid is extracted at 0.5 mL/min and mixed with 0.1 M NaCl aqueous solvent from reservoir 104 also at 0.5 mL/min in the high pressure mixing 'T', yielding a total dilution of 42×, yielding 0.0005 g/mL of combined monomer and polymer flowing continuously through the detector train 105 at 1 ml/min. The slight total excess of 0.05 mL/min entering the LPMC is continuously extracted to waste by the level control pump on the LPMC. The 0.1M NaCl solution largely suppresses interpolymer electrostatic effects.

The signals in the detectors in 105 are combined according to the many published methods by Reed et al. to yield the following quantities: Cumulative and instantaneous weight average molecular polymer weight, cumulative and instantaneous weight average polymer reduced viscosity, cumulative and instantaneous z-averaged polymer radius of gyration, cumulative and instantaneous conversion of each monomer, and average composition drift and distribution. This portion of the system will also alert the experimenter if any unusual process occurs; e.g. the light scattering will immediately detect the onset of microgelation. The conductivity probe in the reactor helps monitor the degree of counterion condensation of the polyelectrolyte chains.

Meanwhile, the pump 12 is extracting ten separate streams of 0.01 ml/min from the reactor 101 and mixing in the 'Ts' 13 with separate aqueous solvents 16 fed into the 'Ts' 13 via the second multi-head pump 15 at a rate of 0.5 mL/min, giving a 51× dilution. The ten aqueous solvents all contain a sub millimolar concentration of pyridine, and each has a different ionic strength, produced by adding NaCl, ranging as follows: 0.0001 M, 0.0005M, 0.001M, 0.005M, 0.010M, 0.050M, 0.1M, 0.25M, 0.5M, 1.0M. The 51× diluted solutions at the varying final ionic strength (taking into account the 0.005M ionic strength before the 51× dilution) each flow through their respective detector train 110, 14; 90 degree light scattering, capillary viscometer, fluorescence cell.

The information obtained from these detectors yields: how reduced viscosity and light scattering intensity (a function of second virial coefficient $A_2$, which is extremely sensitive to ionic strength) react to the different ionic strengths at each moment of synthesis, and the fluorescence detector yield information only if and when micellization occurs. The light scattering and viscosity detectors will also be sensitive to any aggregation, micellization, and significant conformational changes that occur at different states of the reaction and under different ionic strengths.

Hence, one obtains unified, cross-correlated data on the state of the reaction—composition, molecular weight, and other features of the chains being produced via ACOMP front end 103 and ACOMP detector train 105—and on the behavior of the polymers vis-à-vis external stimuli (ionic strength) and vis-à-vis their own tendency to self-organize into micelles or other types of aggregates. This massive, unified data will then allow one both to better understand what characteristics are required to obtain specific polymer stimuli-responsive and self-organizing behavior, and to optimize reactions for producing targeted polymer properties.

A Unified Approach to Understanding Polyelectrolytes by Monitoring their Synthesis and Associated Endproduct Characteristics with Novel Methods ACOMP Background and Summary of Results Automatic Continuous Online Monitoring of Polymerization reactions (ACOMP) yields continuous, model-independent monomer conversion, weight average mass $M_w$ and intrinsic viscosity $[\eta]_w$, monomer conversion, z-average mean square radius of gyration $<S^2>_z$, measures of polydispersity, and average composition drift and distributions, and reactivity ratios (RR) for copolymerization. It does not require size exclusion chromatography (SEC), or other separation techniques, although they have been included for certain applications. The ACOMP principle is to withdraw continuously or substantially continuously a tiny stream from the reactor and dilute it to where detected signals represent properties of individual polymer molecules, not their interactions. Sample stream conditioning prior to detection can include debubbling, filtration, phase inversion, monomer volatilization, etc. Detection typically involves multi-angle light scattering (MALS), viscosity, refractive index (RI) and ultraviolet/visible absorption (UV/Vis), but can also use other detectors, such as ones to detect Mie and dynamic light scattering (DLS), conductivity σ, etc. Massive data sets are captured and analyzed, and ACOMP makes use of the huge storage, computational, and data transfer capabilities available in modern computer and internet platforms.

ACOMP is of interest in three major areas: 1) Formulating and testing kinetic and mechanistic models in order to develop novel materials, reactants, synthetic routes, and processes. 2) Scale-up and process optimization at bench and pilot plant levels. 3) ACOMP, used until now for monitoring, is ready for control of polymer reactions. This can accelerate discovery and development of new polymers, and, at the industrial level, it promises economic benefits in the more efficient use of non-renewable resources, energy, plant and personnel time, improved product quality, and less pollution. Ideally, ACOMP will lead to a new, global standard for the 21$^{st}$ century polymer manufacturing industry.

ACOMP was developed starting in 1998.[1] "Absolute, Real-time Monitoring of Polymerization Reactions" led to expansion of ACOMP and co-developed methods; Automatic Continuous Mixing (ACM) and Simultaneous Multiple Sample Light Scattering (SMSLS). ACOMP has been applied to free radical copolymerization,[2,3,4] step-growth, branching reactions,[5] controlled radical copolymerization (CRP); Nitroxide Mediated Polymerization (NMP),[6,7] Atom Transfer Radical Polymerization (ATRP),[8] and Reversible Addition Fragmentation chain Transfer (RAFT);[9] emulsion,[10] and inverse emulsion polymerization,[11] copolyelectrolyte synthesis,[12,13] and semi-batch[14,15] and continuous reactors.[16] New understanding of basic aspects of these processes has been gained as a result. Validation has been made at each stage on reaction aliquots and endproducts by multi-detector SEC and other traditional equilibrium measurements.

ACM characterizes the conformational, interaction and viscosity behavior of polymers in complex, multi-component systems in equilibrium, using gradients of polymer and other solution components;[17] e.g. ACM can probe dependence of copolyelectrolyte properties on ionic strength, IS, and the valence, symmetry and chemical species of added electrolyte.[18,19]

In the wake of Hurricane Katrina in September 2005, the present inventor's group was invited to the Polymer Sci. & Eng. Dept. at U. Mass., Amherst. A complete ACOMP lab was set up there, highly complementary collaborations were engendered, and the method was quickly extended to several state-of-the-art reaction types and monomers.

The last renewal, after 'repatriation' of the present inventor's group to Tulane, focused on using ACOMP to understand properties of copolymer polyelectrolytes, or 'copolyelectrolytes' by monitoring their synthesis. Accomplishments from this renewal are outlined below.

Basic and Applied Results (Roman Numerals are Associated Publications from the List Immediately Below this Discussion)

Figure 10:
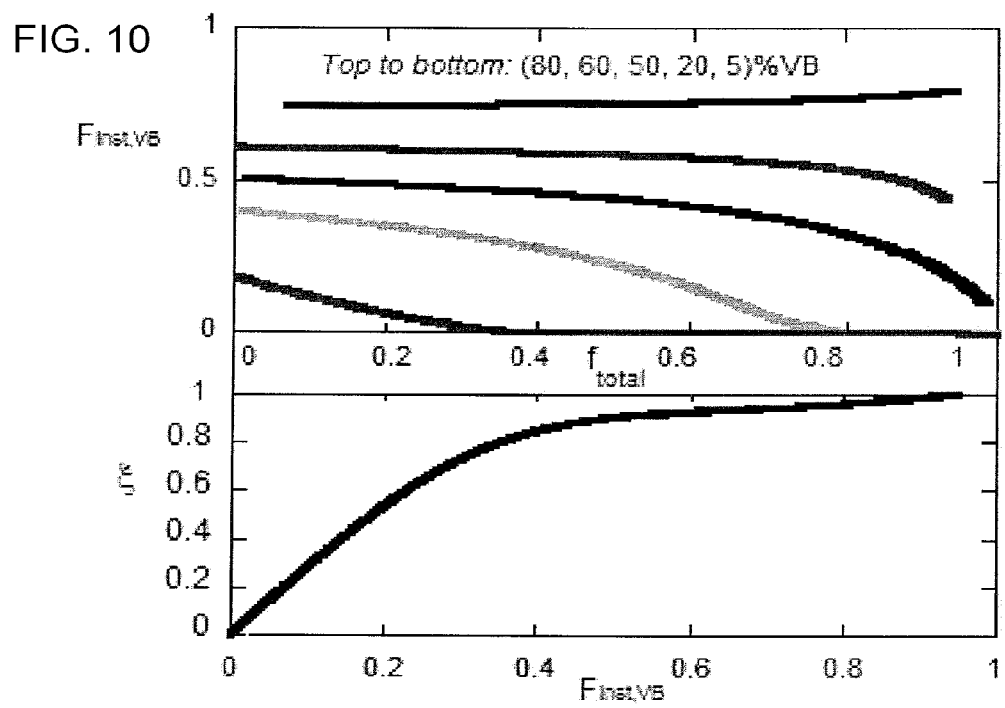
FIG. 10 shows the average instantaneous fraction of vinyl benzene sulfonic acid Na+ form (VB) $F_{INST,VB}$ vs. conversion during VB/acrylamide copolymerization (top); linear charge density $\xi$ v. $F_{INST,VB}$ (bottom)

The project was and continues to be successful (Jul. 31, 2009 end-date) in relating the previously disparate fields of synthetic chemistry of copolymers and the physical chemical properties of polyelectrolytes (v, vi, xii, xvii, xviii). New means for ACOMP to monitor comonomer conversion using full spectrum UV were developed (i), and the traditional problems for determining copolymer molecular weights by light scattering in one solvent were solved using ACOMP's continuous comonomer concentration data and developing a corresponding mathematical formalism (vii). The evolution of solution conductivity, σ was connected to copolyelectrolyte linear charge density ξ (vi, xii, xvii); e.g. FIG. 10 shows the instantaneous fractional compositional amount of cationic comonomer (vinyl benzene sulfonic acid Na$^+$ form, VB) $F_{inst,VB}$, as it is incorporated into a copolymer with acrylamide, for several initial comonomer compositions (top); ξ vs. $F_{inst,VB}$ (bottom), obtained by combining ξ data with conversion, reveals a smooth increase in counterion condensation as $F_{inst,VB}$ increases. ACOMP was also used to monitor postpolymerization reactions,[20] the conversion of polyacrylamide into copolyelectrolyte via base hydrolysis (vi).

As an integral part of this copolyelectrolyte work, new frontiers in monitoring non-ideal aspects of polymerization were opened: ACOMP was applied to quantifying deviations from livingness' in Nitroxide Mediated Polymerization (NMP) (iii) and Reversible Addition Fragmentation chain Transfer (RAFT) (ix). FIG. 11 shows the progression from uncontrolled free radical to living behavior as the amount of RAFT agent is increased, with all other reaction conditions equal. The CRP work set the stage for use of CRP to produce more precisely composed copolyelectrolytes (xviii).

The new methods were applied to 'exotic' monomers with active esters, suited for post polymerization modification (ii), including determination of reactivity ratios (RR). Very fast Ring Opening Metathesis Polymerization (ROMP)[21] reactions were monitored for the first time, with surprising contrasts in 'living' behavior between cyclooctadiene and norbornene derivatives (iv). The high resolution of the new copolymer monitoring method allowed first time monitoring and quantification of the cross-over from decomposition controlled to diffusion controlled radical initiation within single reactions, and among sets of reactions (xiii).

A major advance in emulsion polymerization monitoring was the novel concept of simultaneous dual stream extraction in ACOMP, in which one stream was diluted with aqueous phase to preserve latex particle structures for online Mie scattering/DLS analysis, while the other stream was diluted with aqueous compatible organic solvent (THF) to form a homogeneous solution of polymer, monomer, and surfactant, on which measurements of conversion, $M_w$, etc. are made (xi). FIG. 12 is an example of data rich results on polymer and particle size analysis for the methyl methacrylate (MMA) emulsion polymerization. Industrial level concentrations of up to 35% solids were used. This allows direct cross-correlation between latex particles and constituent polymer properties.

Figure 13:
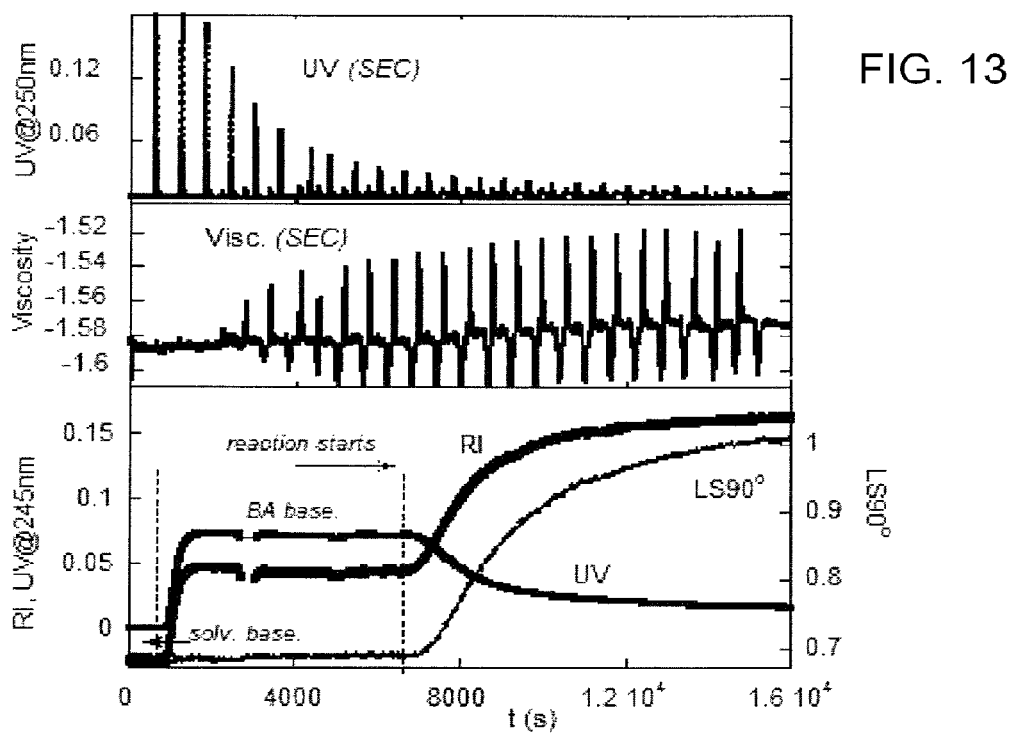
FIG. 13 shows continuous non-chromatographic ACOMP data coupled with continuous discrete, chromatographic data furnished by SEC for the RAFT polymerization of butyl acrylate.

Another ACOMP advance was the coupling of multi-detector SEC to the non-chromatographic, continuous detector stream (xiv). Since the 'front-end' of the ACOMP unit delivers a conditioned, diluted stream to the detectors, an auto-injector feeding a multi-detector SEC system was coupled to the outlet of the detector stream. FIG. 13 shows an example of continuous ACOMP data coupled with auto-collected discrete, chromatographic data for the RAFT polymerization of butyl acrylate. This allowed both the livingness' of the reaction and evolution of the molecular weight distribution (MWD) to be simultaneously monitored.

Central to the current proposal, preliminary work on control of polymerization reactions using ACOMP has been carried out, and is on-going (xv, xvi), and is discussed further below.

The advantages of ACOMP have become better known in the Polymer Science & Engineering community and two invited articles reviewing the field were produced during this period (viii, x).

PUBLICATIONS i. *Macromolecules*, 39, 5705-5713, 2006.
ii. *Macromolecules*, 39, 8283-8292, 2006.
iii. *Macromolecules*, 39, 8213-8215, 2006.
iv. *Macromolecules*, 40, 444-451, 2007.
v. *J. Phys. Chem. B*, 111, 8560-8566, 2007.
vi. *Macromolecules*, 40, 4409-4413, 2007.
vii. *Macromolecules*, 40, 8040-8049, 2007.
viii. *Polymer International* (invited), 57, 390-396, 2008.
ix. *Macromolecules*, 41, 332-338, 2008.
x. *Macromolecular Symposia*, (Modelling, Monitoring and Control of Polymer Properties), 271, 15-25, 2008.
xi. *Macromolecules*, 41, 2406-2414, 2008.
xii. *J. Phys. Chem. B*, 112, 14597-14608, 2008.
xiii. *Macromol. Chem. Phys.*, 209, 24, 2463-2474, 2008.
xiv. *J. Appl. Polym. Sci.*, 13, 190-198, 2009.
xv. T. Kreft, W. F. Reed, "Predictive control and verification of conversion kinetics and polymer molar mass distributions in semi-batch reactions", European Polymer J., in press
xvi. T. Kreft, W. F. Reed, "Predictive control of average composition and molecular weight distribution (MWD) in semi-batch free radical copolymerization reactions", Macromolecules, in press
xvii. T. Kreft, W. F. Reed, "Cross-over from non-condensed to counterion condensed regimes during free rad. polyelectrolyte copolym. under high composition drift conditions", J. Phys. Chem. B, web edition, May 22, 2009.
xviii. L. Zheng, A. M. Alb, W. F. Reed, 'Online monitoring of reaction kinetics in the case of copolymeric polyelectrolytes produced by RAFT polymerization—novel approaches', in preparation.

Relation of Completed Work to Proposed Work

The completed and ongoing work has expanded ACOMP applications into most major classes of polymerization, with the recent focus on copolyelectrolytes, and extensions to living and heterogeneous phase reactions. Each new application helps solve basic polymer science problems. The proposed work will develop '$2^{nd}$ generation ACOMP' as it faces wholly new challenges; moving beyond monitoring to reaction control, to produce polymers 'on-command', and extending the ACOMP platform to monitor, and later to control, the stimuli-responsiveness of polymers. This work has basic dimensions dealing with kinetics and mechanisms of polymerization reactions, especially as contrasted in homogeneous and emulsion phase reactions, and the thermodynamics of self-organization in solution of polymers, and applied aspects, requiring further novel instrumentation and methodology development. ACM will be important in characterizing phase transition and self-organizing characteristics of copolymer endproducts.

Project Description

Online Monitoring and Control of Polymerization Reactions with Application to Stimuli Responsive Polymers Introduction The sophistication of polymeric materials is increasing rapidly as new synthetic routes and processes are developed. Improved and often transformational polymers are found in high performance aeronautical and marine coatings, fuel cell membranes, sensors, nanostructure components, pharmaceuticals, biomedical materials, water treatment, paper making, oil recovery, and biomimetic agents, and self-healing materials. Many such polymers are stimuli responsive.

At the same time, new analytical approaches are required to solve basic and applied problems, optimize processes, and provide means of reaction control. Furthermore, means are needed to monitor copolymer characteristics, including composition and molecular mass distributions,[22,23,24] RR,[25,26,27] and complex phenomena associated with polymers, such as micellization, aggregation and other supramolecular assemblies, and phase and surface behavior.[28,29,30,31,32,33,34,35] Currently, post-synthetic analysis relies on tedious cross-fractionation and other coupled techniques. These include calorimetry, densimetry,[36] liquid chromatography,[37] temperature rising elution fractionation,[38,39,40,41] crystallization fractionation,[42] SEC alone,[43,44] SEC/NMR,[45] SEC/

MALDI,[46] and SEC/thin layer chromatography,[47,48,49] and temperature gradient interaction chromatography.[50] Little information concerning the evolution of polymer characteristics can be gleaned by these approaches and there is no opportunity for control. ACOMP follows kinetics, composition drift, and evolution of average composition distribution, molar mass, and [η] distributions. The polymer is hence 'born' characterized. Importantly, information-rich ACOMP results also provide a more complete database for polymer scientists in the broader community involved in modeling and reaction engineering.

With its broad range of monitoring applicability secured, a '$2^{nd}$ generation ACOMP' will be created to control reactions by both predictive and active feedback approaches, and expand to monitoring and control of polymers that have, or acquire during synthesis, specific stimuli responsiveness. Such polymers include those whose properties change with changing environmental factors, such as temperature, light, pH, solvent quality, presence of specific molecules, etc. Potential applications of these materials make them an exciting interface between chemical and biomolecular engineering, chemistry, and physics. The onset or change of stimuli responsiveness, such as conformational transformations, ability to interact with target molecules, copolymer micellization, etc. have complex relationships to polymer mass, architecture, copolymer distribution, 'blockiness', sequence length distributions, etc. This work takes the novel approach of monitoring when onset or changes of stimuli responsiveness occur during synthesis, providing a powerful new tool for understanding the underlying polymer physics, and controlling and manipulating polymer structure/function relationships.

The present inventor uses the term '$2^{nd}$ generation ACOMP' because it takes the next steps in advancing ACOMP, by developing new reaction control strategies and an expanded platform for monitoring, understanding, and controlling the evolution of stimuli responsive polymers during synthesis. At the same time that ACOMP's ability to address basic science questions is growing, its use of massive data storage, analysis, and transfer is becoming correspondingly more sophisticated. The present inventor is involved in a range of industrial sector projects whose specificity complements the basic science scope of the present invention. Projects include determining reaction kinetics and properties of synthetic polypeptides, elastomers, graft copolymers, copolyelectrolytes for water treatment, acrylate copolymers in emulsion, etc.

The present inventor has broad experience in carrying out many types of polymer syntheses, including CRP methods; NMP,[6,7] ATRP,[8] and RAFT.[9] The present inventor has access to traditional methods such as FTIR, DSC, NMR, and a complete suite of cryogenic imaging instruments. New ACOMP results are constantly validated with multi-detector SEC and other methods.

Background on Approaches to Polymerization Reaction Control

The development of more sophisticated polymers requires corresponding advances for controlling the polymerization reactions themselves, especially as regards control of polymer molecular weight, copolymer composition, architecture, and stimuli responsiveness.

The lack of on-line measurement of polymer properties is usually the main problem in closed-loop control of polymerization reactions. Hence open-loop methods are frequently used. The controllers employed in closed-loop methods use some on-line measurements, but none have had continuous or substantially continuous streams of co-conversion, molecular weight and other pertinent data available, precisely the type of massive data stream provided by ACOMP.

There is extensive work on measuring, controlling and engineering more robust polymerization reactors.[51] Much attention has centered on maintaining pressure, temperature, level and flow in the reactor.[52,53,54] Online composition measurement techniques, include FTIR,[55] NIR, Raman,[56] calorimetry,[57] and gas chromatography. There are typically serious problems with drift and bias in the empirical and inferential models used for data interpretation, and fouling of in-situ probes. Controlling composition during copolymerization includes the Kalman filter method, based on linear approximation of the nonlinear process,[58] but it has stability and convergence problems.[59,60] Nonlinear methods have hence been developed,[61,62,63,64,65] as well as Linear and non-linear Model Predictive Control algorithms.[66,67,68,69,70,71,72,73,74]

The semi-batch approach, for selective reagent feed policies to the reactor has been extensively elaborated,[75] especially for emulsion polymerization and copolymer composition,[76,77,78,79,80] including for CRP.[81,82] Composition and MWD control was achieved in emulsion copolymerization in an open-loop method, maintaining the ratio of comonomers.[83,84]

Efforts to control $M_w$ have been reported.[59,78,85,86] Usually, the main difficulty in controlling $M_w$ is the lack of on-line sensors. In general, molecular weight is controlled by manipulating the concentration of monomer, initiator, or chain transfer agent, CTA.[87,88,89,90,91,92]

Background on Stimuli Responsive Polymers

Precisely engineered complex and architecturally sophisticated polymers that can perform more 'intelligent' functions than traditional polymers will dominate the frontier of advanced polymeric materials in the $21^{st}$ century. They can micellize, aggregate, and respond to stimuli, such as temperature, light, solvent polarity, different solvents and solvent mixtures, the presence of specific agents, multivalent ions, proteins, anti-bodies, receptors, etc.[93,94,95,96,97] Applications include sensing, encapsulation and release of agents (e.g. drugs), micropatterning, bioconjugated polymers for medical applications, etc.[98,99,100] There is considerable interest in 'fine tuning' polymers to have well behaved phase transitions and interaction properties.[101,102,103] Such transitions are of basic and applied interest. They arise from the thermodynamics of complex systems, often involving cooperative behavior. These transitions depend on many factors, such as pH, IS, solvent type and polarity, solvent chaotropicity or cosmotropicity, temperature, irradiation by light, and addition of interacting agents (e.g. small molecules, dyes, etc.), as well as on the molecular weight distribution (MWD) and copolymeric composition and microstructure of the polymers themselves. Other examples concern the many types of associations that can take place between polymers and other polymers, micelles, emulsions, vesicles, liposomes, proteins, polypeptides, etc. These often involve formation of supramolecular structures promoted by electrostatic, hydrophobic, depletion, and other forces.[104,105,106,107,108,109,110,111,112,113]

Current methods for relating polymer characteristics to their stimuli responsiveness are cumbersome and inefficient. They normally involve synthesis of a series of end-products that are then tested for stimuli responsiveness. The mere preparation of polymeric test products can be disproportionately time-consuming, and require such steps as precipitation, purification, freeze-drying, re-dissolution, dialysis, etc. In contrast, the ACOMP approach has proven successful in a wide variety of contexts and avoids these process steps by substituting 'fluid-fluid' sample handling; reactor fluid is continuously extracted, diluted and conditioned to produce a continuously measurable sample stream. No intermediate solid phases are used, and the often high levels of dilution (up to factors $10^4$x) can effectively even change solvents. Such extraction/dilution/conditioning typically occurs on times of tens to hundreds of seconds.

Stimuli responsiveness testing can involve high throughput screening of end-products, such as multiple well, channel plates, or continuous gradient devices. Spectroscopic or other detection of transitions can be made.[114,115] These methods, however, have no means of determining when during synthesis the polymer's stimuli responsiveness begins to appear. It would take many more reactions to explore even a finite number of compositions and MWD, whereas the during-synthesis method proposed below allows continuous determination, in single experiments, of polymer characteristics required for sharp or gradual changes in stimuli responsiveness.

Outline of Principal Project Dimensions

Below is an outline of an embodiment of the present invention. The numbered sections are for convenience only, since the project is highly integrated and the issues are interwoven throughout. For illustration n-isopropyl acrylamide (NIPAM) and comonomers will be used as reference reagents to show the interconnectedness from control principles, to different mechanisms and phases of polymerization, to stimuli responsiveness. The project is not restricted to NIPAM and its comonomers, however. One important dimension of the project is establishing feasibility of new analyses, methods, and instrumentation with reference reagents.

A. Control

Predictive Control in Semi-Batch Homo- and Copolymerization Reactions
i. Control of $M_w$ in Homogeneous Phase Free Radical Homopolymerization and of $M_w$ and Particle Size in Corresponding Emulsion Phase Reactions This stage focuses on quantitative predictions and online verification of targeted conversion kinetics and $M_w$ during free radical homopolymerization under semi-batch reagent feed to the reactor. Detailed kinetic parameters furnished by ACOMP provide the quantitative basis for predictive control, and, subsequently, ACOMP serves immediately as a means of online validation of the predicted reaction trajectories. Reagent feeds need not be constant and can be tapered and modulated in calculable ways to obtain polymers 'on-command'. An important theme is the contrast in basic kinetics and mechanisms between homogeneous phase and corresponding emulsion phase reactions. Far less has been published on control of $M_w$ in emulsion polymerization than on particle size distributions.

Figure 14:
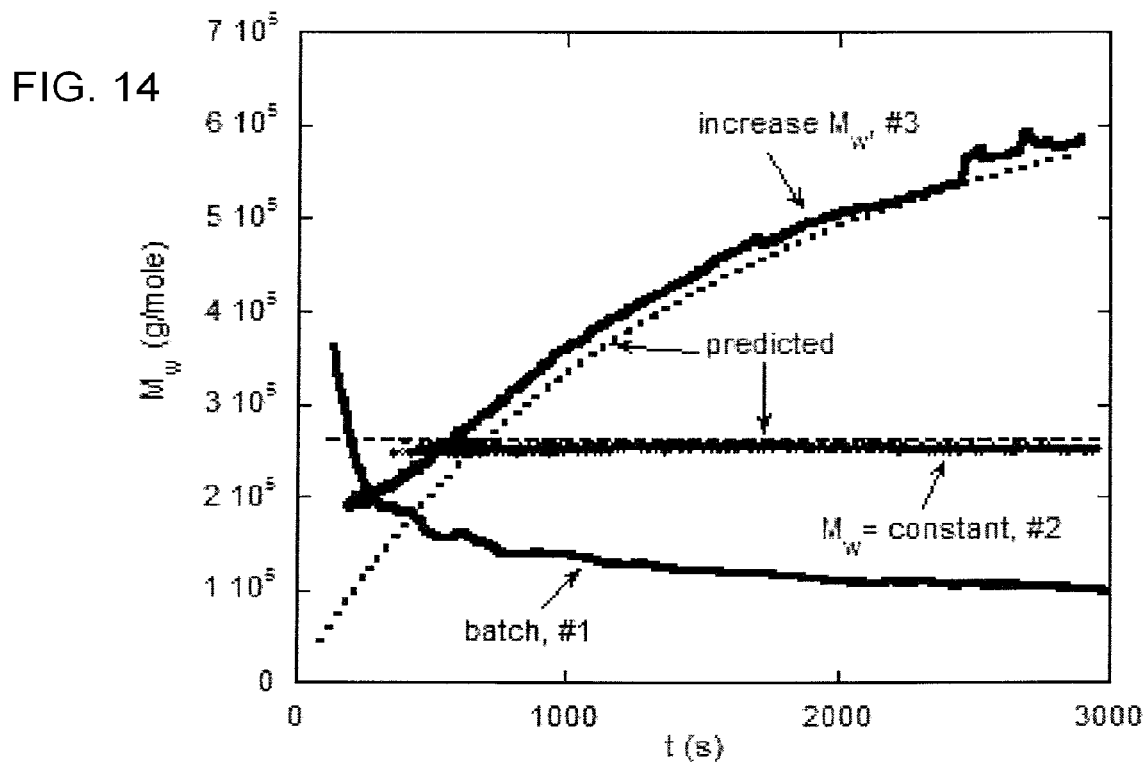
FIG. 14 shows predictive and experimental $M_w$ trends for the semibatch acrylamide polymerization (#2, #3); #1: $M_w$ for a batch reaction.

The present inventor and others have established formalisms combining reaction kinetics with time dependent reactant flows into the reactor. FIG. 14 shows an example of predictive control for the solution polymerization of acrylamide, where monomer addition rate was computed and set to achieve desired $M_w$ trends (Kreft, Reed, European Polymer Journal, in press). Experimental and predicted $M_w$ trends are shown for semi-batch reactions, where $M_w$ was increased in one and held constant in the other. In contrast, $M_w$ decreases in a batch reaction. This predictive approach will be used as an Ansatz for reaction trajectory estimation. NIPAM will be one of the first candidates for this part.

Considering the broad applicability of polymer latexes in nanotechnology, biomedical and other areas, work will next focus on predictive control in the synthesis of latexes with desired size and $M_w$ properties.[116,117,118,119,120,121,122,123] Portions of the control strategies established for homogeneous phase will be adapted to emulsion semi-batch reactions to obtain these properties.

The emulsion semi-batch methods are predicated on manipulating monomer 'starved' and 'flooded' regimes,[124,125,126] dictated by the combination of inherent conversion kinetics, reagent flow rates, and reactor volumes. The multiple detection ACOMP platform yields data rich results on which more refined models can be constructed.

In this section, the method of Alb and Reed[10] to simultaneously monitor particle size distribution, $M_w$ and conversion will be applied to predictive control of these characteristics. Addition of dynamic light scattering (DLS) detection (BIC nano-DLS) to the online monitoring, with good size resolution in the 1-1000 nm range will complement the Mie scattering in current use with range >100 nm.

Preliminary results (Alb/Reed) on $M_w$ and monomer/polymer concentrations for MMA-starved semibatch polymerization have been obtained and the transition between monomer starved and flooded regimes have been directly monitored while feeding reagents into the reactor under different flow schemes.

In this part, the effect of feed rate on approach to quasi-steady state, latex particle characteristics, and polymer $M_w$ and $[\eta]_w$ and their correlation to the monomer conversion kinetics will be quantified and compared with existing models,[118,120,121,124,125] and serve as the basis for this group's own modeling efforts. This type of approach to the detailed inter-relationship of kinetics, particle size distribution and polymer MWD will form the basis for designing predictive routes to targeted latex and polymer properties. This part will also study monomers with very different aqueous solubility, such as BA and methyl acrylate (MA) to quantify effects of monomer partitioning on particle size, polymer $M_w$ and conversion kinetics.
ii. Composition and $M_w$ Control in Copolymerization Building on part i, semi-batch operation will be extended to control of composition distribution and $M_w$ in the case of copolymerization. Guided by comonomer conversion kinetics and RR from ACOMP, it will be possible to calculate the reagent feeds required to produce desired composition drifts, and hence composition distributions. Good candidates are NIPAM and VB. Because there is usually an $M_w$ dependence associated with composition, in addition to reaction conditions, it will be possible to target both $M_w$ ranges and composition distributions. Initial work will be in homogeneous phase.

Figure 15:
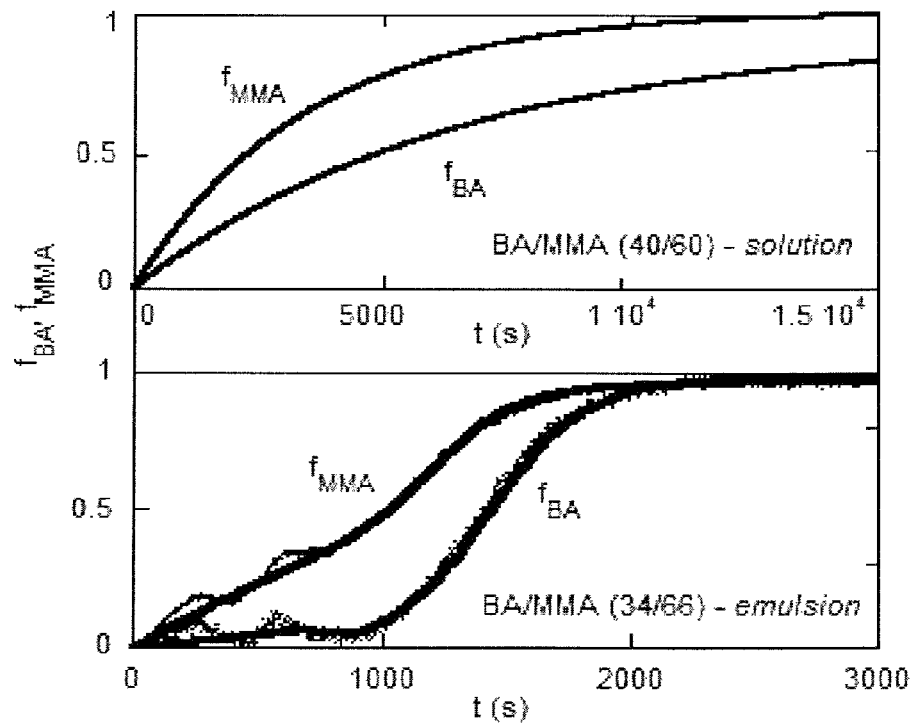
FIG. 15 shows comonomer ACOMP conversion from BA/MMA copolymerization reactions in emulsion and solution.

Applying semi-batch to control emulsion copolymerization reactions is much more challenging for both fundamental and practical reasons; e.g. different degrees of comonomer aqueous solubility lead to different partitioning among dynamically evolving aqueous, micellar, droplet, and latex phases, while exothermicity at high solids leads to non-isothermal polymerization kinetics. FIG. 15 is an example of comonomer ACOMP conversion data from a 34/66 BA/MMA emulsion copolymerization (below), compared to data from a 40/60 BA/MMA solution phase copolymerization (above) (Alb, Reed, prelim. results). The first order co-conversions in solution stand in dramatic contrast to the inflected, multi-phase co-conversion in emulsion. In such complicated systems, the evolution of each component during the reaction plays an important role and can change the multicomponent system's dynamic balance.

To achieve desired comonomer composition, copolymerization reactions will be performed under different feed policies. Comomomers with different RR and degrees of hydrophobicity, such as NIPAM and styrene will be used in these reactions. Resulting latex particles exhibit temperature responsiveness.[127] The present inventor's research group has obtained promising preliminary results from the NIPAM/styrene soap-free emulsion copolymerization. ACM and DLS will be used for a complete validation of the endproducts in terms of colloidal properties, stability vs. pH, ionic strength and temperature.

Few studies treat simultaneous control of $M_w$ and particle size distributions.[128,129] Here, the effect of CTA on reaction kinetics, particle nucleation, radical partitioning, and hence on $M_w$ distribution and on the polymerization rate will be investigated. A database of reaction parameters from experiments in batch will be used in the calculation of the optimal feed schemes for comonomers and CTA (e.g. tertdodecyl mercaptan and dodecanethiol) to be followed during semi-batch reactions to achieve desired composition and MWD copolymers.

iii. Composition and $M_w$ Control of Living Copolymerization (RAFT)

Results of predictive semi-batch control developed in part ii will help guide control of composition gradients of polymers produced by CRP. The fact that conversion kinetics and RR are usually similar for a given comonomer pair in corresponding 'living' and free radical copolymerization lets the CRP work build on the latter.

Figure 16:
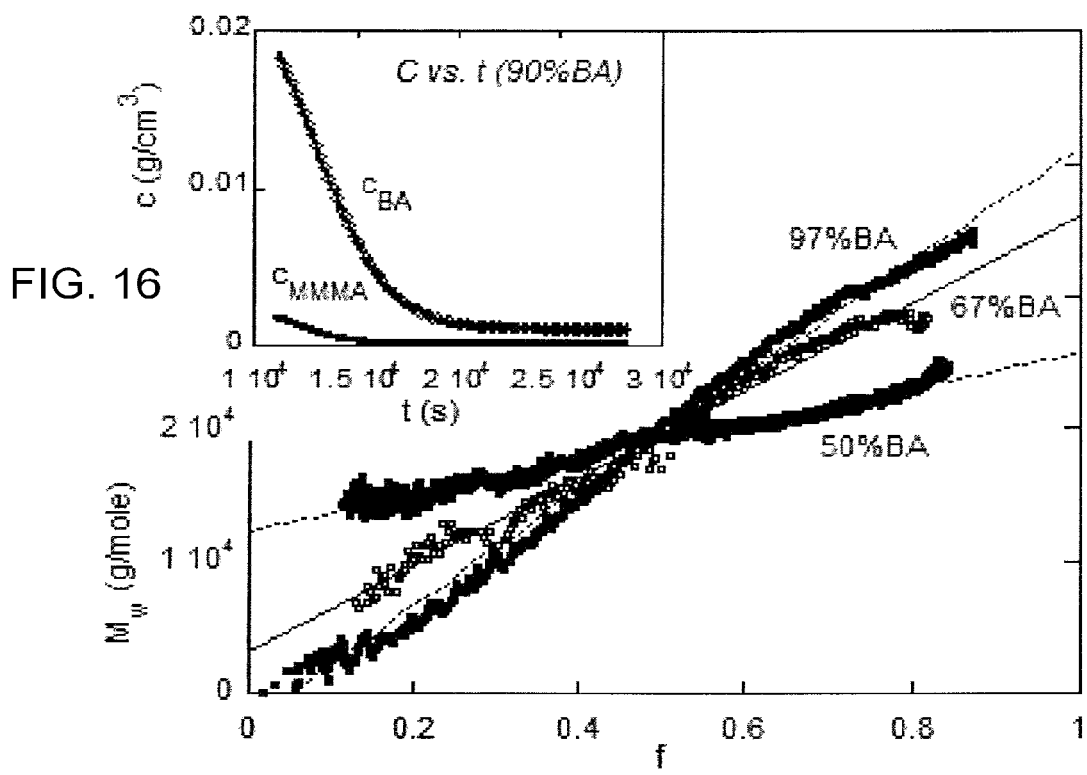
FIG. 16 shows that ACOMP monitors deviations from livingness in $M_w$ for BA/MMA copolymerization by RAFT, Inset: $C_{BA}$ and $C_{MMA}$.

CRP allows gradient copolymers to be produced, not possible in classical radical polymerization, in which the composition profile changes along the chain, leading to distinctive material properties.[130,131,132,133,134,135,136] ACOMP joins other methods[137,138,139,140,141] which study and quantify deviations from 'livingness' in RAFT kinetics under different conditions. E.g. FIG. 16 shows the comonomer incorporation (inset) and deviations in $M_w$ behavior during the BA/MMA copolymerization by RAFT (Alb, Reed, prelim. results). The main physical quantities, $M_w$, composition distribution, etc. are provided in a single experiment.

Comonomer pairs with widely separated RR (e.g. N-(2-hydroxypropyl) methacrylamide and N-methacryloyloxy-succinimide) will be exploited to synthesize copolymers with broad, predicted compositions. The semi-batch approach with calculated rate of addition of the more reactive comonomer will allow constant copolymer composition to be maintained or other desired composition profiles to be produced. Again, the ability of ACOMP both to furnish the kinetic basis for quantitative predictions and to provide immediate online validation of the predictions during subsequent reactions is of decisive importance in this approach.

RAFT Emulsion Polymerization

Adaptation of CRP to emulsion has been made with varying degrees of success.[142,143,144] RAFT is especially suited for heterogeneous aqueous systems, since its reaction conditions are as robust as typical free radical polymerization.[145,146,147,148,149,150,151,152] Promising preliminary ACOMP studies in this group were made monitoring the RAFT polymerization of BA in emulsion, based on the procedure established at CSIRO.[146] Work here will focus on trying to achieve the most living character possible in the reactions, hence improving MWD control. The approach will be used on different monomers (e.g. MA, BA, styrene) while studying how different factors such as chain dimensions, monomer aqueous solubility, monomer feed rate, the transport of RAFT agents to polymerization sites, the radical entry and exit in and from the latex particles, colloidal stability, affect the living character of the reaction and the particle size.

Active Control in Homo- and Copolymerization Reactions

While active control is not a primary focus of this proposal, some aspects to be developed will have important consequences for both on-command polymer synthesis and in the polymer stimuli responsiveness studies described below.

iv. Conversion Endpoint/Trigger Control.

Precise monitoring and control of reaction conversion, especially in the final phases, are often needed: environmental and safety restrictions frequently limit the amount of residual monomer in a polymer lot (<10 ppm is typical); very high conversion is often required before proceeding to form subsequent blocks in multi-block copolymers; efficient use of reactors requires accurate reaction timing; in semi-batch or continuous reactors, the steady state conversion level for production rate and reagent recycling must be known; in changeover from one product composition to another in continuous reactors, it must be known when the new composition is reached.

As first steps in automated control of free radical homopolymerization, both in batch and semi-batch, conversion will be monitored and the reaction automatically terminated when the endpoint is reached. Tight limits on residual monomer will be targeted, with the following proposed strategy; Tandem full spectrum UV detectors will be used, one with a 0.01 cm pathlength cell that quantifies conversion up to 99%, followed by another with a 1 cm cell that will be saturated during most of conversion, but will then come on scale at >99% conversion, and monitor residual monomer down to 10's of ppm. The full spectrum will allow distinguishing between residual absorption and small admixtures of scattering. Automatic control will involve quenching the reaction, reducing temperature, halting any reagent feeds, and returning detector flows to pure solvent. The present inventor's lab has multiple resources for instrument control, computer programming and graphical user interface development for this purpose.

This strategy will be extended to living multiblock copolymerization. A second block of copolymer will be initiated automatically upon reaching a conversion setpoint whereupon a signal will start the flow of the second monomer and change any other conditions necessary; e.g. extra initiator, RAFT agent, solvent, etc. This process can be extended to multi-blocks.

Figure 17:
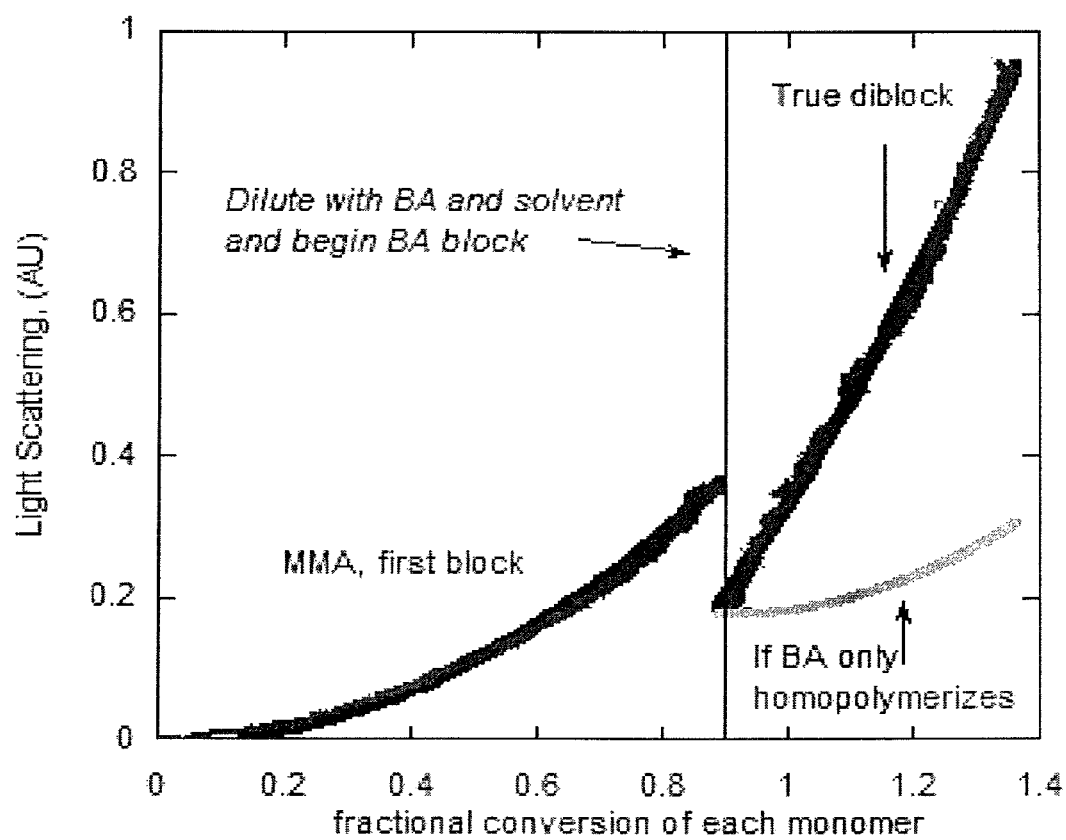
FIG. 17 shows experimental and theoretical light scattering signatures for the MMA/BA diblock copolymerization by RAFT.

The ACOMP data can distinguish when the second block is being properly polymerized to the first or is merely homopolymerizing. E.g. in FIG. 17 (Alb, Reed, prelim. results) experimental and theoretical (gray curves) light scattering signatures are compared. The MMA first block follows the living prediction, with no transfer or termination side reactions, and the second BA block is successful, following the prediction for a true diblock. The gray line below shows what would be obtained by BA homopolymerization, if it failed to add to the pMMA block.

B. Monitoring and Controlling Evolution of Stimuli Responsiveness During Polymer Synthesis It is proposed here that the evolution of stimuli responsiveness can be monitored vs continuously changing $M_w$, composition, and other characteristics (e.g. polyelectrolyte ξ, polymer branching, cross-linking, 'click' reactions, etc.)

as polymers evolve during their synthesis. This approach will allow stimuli responsiveness to be assessed on the equivalent of a continuum of endproducts. The proposed new $2^{nd}$ generation ACOMP configurations preferably will still also include the basic detector train for determining $M_w$, copolymer conversion, etc. but high throughput multi-detectors will be added to probe stimuli responsive effects.

This work will develop the proposed method focusing on a single type of stimuli responsiveness, Lower Critical Solution Temperature (LCST). It will then be vigorously employed to investigate the basic physics and many factors controlling polymeric LCST.

This method, if successful, promises broad impact for accelerating the discovery and development of stimuli responsive polymers. It will be widely applicable and be suited to most reactions: living, post-polymerization modifications, step growth, free radical chain growth, grafting, branching, bioconjugation, etc. It will also be useful for batch, semi-batch, and continuous reactors. It should provide a rapid means of optimizing polymer properties to carry out desired stimuli responsive tasks, by quantifying how stimuli responsiveness evolves. Once it is known when during synthesis a polymer achieves desired stimuli responsiveness, polymers of precisely those characteristics at that point of synthesis can then be targeted as end products in subsequent experiments or manufacturing.

As described, stimuli responsiveness can be manifested in many ways; conformational changes such as coil to globule (e.g. LCST) and helix to coil, micellization, whether uni- or plurimolecular, aggregation, whether reversible or not, ability to associate with specific agents, etc. While methods exist for observing polymeric stimuli responsiveness, e.g. turbidity, fluorescence, conductivity, surface tension, light scattering, circular dichroism, and birefringence,[101,153,154,155] no during-synthesis methods exist, to the present inventor's knowledge, which simultaneously measure stimuli responsiveness and polymer properties, such as MWD and composition.

In the focus of this work, high throughput light scattering detectors will be coupled to the system to make multiple, simultaneous measurements. SMSLS,[156,157] a flexible family of relatively inexpensive scattering instruments developed by the present inventor is ideally suited for this and will be developed accordingly. SMSLS cells can be fabricated in-house. Holding each flow cell in series at different, increasing temperatures will allow determination of the LCST for as many $M_w$ and compositions of polymer as there are SMSLS flow cells. Light scattering is exquisitely sensitive to even the slightest amount of aggregation, so that the LCST will be immediately detectable in highly diluted sample streams.

In another approach, the effect of different solvents on the LCST of evolving polymers during synthesis will be tested simultaneously using a multi-head peristaltic pump for multiple, tiny extraction flows from the reactor, with dilution in separate mixing chambers using another multi-head peristaltic pump drawing from multiple solvent reservoirs. The SMSLS flow cells, now held at the same temperature, will then detect the effect of each different solvent on the LCST. For example, the effect of IS on NIPAM LCST is well known.[101] For more complex, NIPAM-based copolymers and copolyelectrolytes, solvent effects will be even stronger.

Specific Experiments Both to Develop the Method and Study Underlying Polymer Physics Polymers with LCST will be used first for developing the method. NIPAM's LCST is around 32° C. Different techniques are used to produce polymers with LCST[158,159] and other stimuli responsiveness; pH, IS, UV, etc.[160,161]

After proving feasibility of the method with NIPAM under free radical homopolymerization, LCST dependence for low molecular weight polymers under RAFT polymerization will be quantified. LCST is only dependent on polymer degree of polymerization (DP) up to fairly low values (on the order of DP~$10^2$). RAFT allows a controlled, linear increase of DP (e.g. FIG. 11), thus allowing the method to closely test LCST dependence on low, continuously varying DP.

Next, copolyelectrolyte LCST study will provide intriguing new features and physics. A current project on which the inventor is working has developed tools for complete polyelectrolyte characterization during synthesis, including distribution. The above proposal portion on control will allow predictively harnessing composition drifts to produce widely different composition and property paths during synthesis. Having determined a control paradigm for VB (charged) and NIPAM (neutral) in the above portion, the effect of both large composition drift and $\xi$ distribution on the LCST can be explored. Increasing the fraction of VB will increase the LCST due to higher copolyelectrolyte solubility. Additionally, decreasing solvent ionic IS should likewise increase LCST due to increased interchain electrostatic excluded volume. The behavior of the LCST vs $\xi$ distribution and IS is a little explored field, but will allow better understanding of the underlying LCST physics and how LCST can be manipulated through targeted synthesis.

The advantages of RAFT, together with predictive and automated endpoint control methods described above, will be exploited here to synthesize both block and gradient copolymers with LCST, such as NIPAM with other acrylamide derivatives (e.g. N,N'-dimethylacrylamide, DMA).[162] The goal is to better understand how changes in the polymer architecture and relative block and gradient composition affect the LCST. Selective solvents can be used to distinguish the behavior of the two species in the copolymer.

Conceptual Flow Chart of how NIPAM Will Interconnect to the Various Portions of this Project

| Emphasis1 | Emphasis2 | Purpose | Type | Mechanism | Comonomer |
|---|---|---|---|---|---|
| $M_w$ control | Feasibility | Establish control paradigm & On-command polymers | Homopol. | Free rad. | X |
| " | " | " | " | " | X |
| $M_w$ control | Feasibility | Establish control paradigm & On-command polymers | Homopol. | Living | X |

-continued

| Emphasis1 | Emphasis2 | Purpose | Type | Mechanism | Comonomer |
|---|---|---|---|---|---|
| $M_w$/composition control | Polyelectrolyte physics | Establish control paradigm & On-command polymers | Copolym. " | Free rad. Living | VB VB |
| $M_w$/comp./ Particle size | Kinetics | Establish control paradigm & On-command polymers | Copolym. | Free rad. | Styr. |
| Feasibility | | Establish stimuli responsive methodology | Homopol. | Free rad. | X |
| Origins of LCST | | LCST dependence on $M_w$ | Homopol. | Living | X |
| Origins of LCST | | LCST dependence on composition | Copolym. | Living | DMA |
| Origins of LCST | Polyelectrolyte physics | LCST dependence on Composition & ionic strength | Copolym. | Free rad. | VB |

PART NUMBER DESCRIPTION

1 Polymerization reactor
2 Optional reactor probes
3 ACOMP front end
4 Solvent reservoir
5 ACOMP detector train
6 Microcomputer control
7 Optional auto-SEC
8 Waste vessel
9 Desired dilution/conditioning
10 Multiple detection modules
11 Multiple detection modules
12 Multi-head peristaltic pump
13 Mixing 'Ts'
14 Multiple detection modules
15 Second peristaltic pump
16 Dilution reservoirs
101 Jacketed polymerization reactor
102 Reactor conductivity sensors
103 ACOMP front end
104 Solvent reservoir
105 The ACOMP detector train
106 Microcomputer control
107 Auto-SEC
108 Waste vessel
110 Static light scattering cells The following is a list of acronyms used herein and their descriptions:

ACRONYM DESCRIPTION

A/D analog to digital
ACM Automatic Continuous Mixing
ACOMP Automatic Continuous Online Monitoring of Polymerization reactions
ATRP Atom Transfer Radical Polymerization
BA butyl acrylate
BIC Brookhaven Instruments Corp.
CCD Charge coupled device
CRP Controlled radical copolymerization
CSIRO an Australian research center
CTA Chain transfer agent
DLS Dynamic light scattering
DMA N,N'-dimethylacrylamide
DP Degree of polymerization
DSC Differential scanning calorimetry
FTIR Fourier transform infrared spectroscopy
GPC Gel permeation chromatography
GUI Graphic user interface
HPLC High pressure liquid chromatography
IS Ionic strength
LCST Lower critical solution temperature
LPMC Low pressure mixing chamber
MA methyl acrylate
MALDI Matrix assisted laser desorption ionization
MALS Multi-angle light scattering
MMA methyl methacrylate
MWD Molecular weight distribution
NIPAM n-isopropyl acrylamide
NMP Nitroxide Mediated Polymerization
NMR nuclear magnetic resonance
PolyRMC Tulane Center for Polymer Reaction Monitoring and Characterization
RAFT Reversible Addition Fragmentation Chain Transfer
RI Refractive index
ROMP Ring Opening Metathesis Polymerization
RR Reactivity ratios
SEC Size Exclusion Chromatography
SG-ACOMP Second generation ACOMP
SMSLS Simultaneous multiple sample light scattering
THF Tetrahydrofuran
UV/Vis Ultraviolet/visible absorption
VB vinyl benzene sulfonic acid Na+ form All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A device for monitoring the synthesis of a polymer comprising (a) a reactor for synthesizing the polymer; (b) at least two detectors that each detect a property of the polymer, each detector being the same type of detector, and each detector detecting the same property of the polymer at a different condition; and (c) a component comprising an extraction stage that extracts a sample from the reactor for delivery to each of the at least two detectors, said sample comprising the polymer.

2. The device of claim 1, wherein the component further comprises a dilution stage that dilutes the sample after extraction.

3. The device of claim 1, wherein the component further comprises a conditioning stage that conditions the sample after extraction.

4. The device of claim 3, wherein the conditioning stage conditions the sample after extraction and dilution.

5. The device of claim 1, further comprising a size-exclusion chromatographic separator.

6. The device of claim 5, wherein the chromatographic separator is positioned after at least one of the at least two detectors.

7. The device of claim 6, wherein the chromatographic separator is positioned after each of the at least two detectors.

8. The device of claim 1, wherein the at least two detectors are serial to one another.

9. The device of claim 1, wherein the at least two detectors are parallel to one another.

10. The device of claim 1, comprising at least three detectors.

11. The device of claim 10, wherein each detector is the same type of detector, and each detector detecting the same property of the polymer at a different condition.

12. The device of claim 10, wherein at least one detector detects a different property of the polymer.

13. The device of claim 10, wherein two of the detectors are serial to one another or two of the detectors are parallel to one another.

14. The device of claim 1, wherein the property of the polymer that each of the at least two detectors detect is selected from the group consisting of light scattering, ultraviolet/visible absorption, refractometry, viscometry, conductivity, pH, polarimetry, turbidity, fluorescence, circular dichroism, and birefringement.

15. The device of claim 1, wherein each condition is selected from the group consisting of temperature, ionic strength, pH, solution composition, and radiation.

16. The device of claim 15, wherein the solution composition comprises one or more of a salt, a dye, a small molecule, a pigment, a nanoparticle, a surfactant, and a second polymer.

17. A method of monitoring polymerization of a polymer comprising
(a) synthesizing a polymer in a reactor under a first set of reaction parameters;
(b) extracting a sample of the polymer from the reactor during the synthesis;
(c) flowing the sample through at least two detectors;
(d) detecting a property of the polymer at each of the at least two detectors to produce at least two signals, each detector being the same type of detector, and each detector detecting the same polymer property at a different condition; and
(e) analyzing the signals to determine the polymer property at each condition.

18. The method of claim 17, wherein the sample is flowed through the at least two detectors serially.

19. The method of claim 17, further comprising separating the sample into a first portion and a second portion before the flowing step, wherein the first portion flows through a first detector of the at least two detectors and the second portion flows through a second detector of the at least two detectors, the first detector and the second detector in parallel.

20. The method of claim 17, further comprising modifying the first set of reaction parameters to a second set of reaction parameters, based on the analysis of the signal from each detector, and synthesizing the polymer in the reactor under the second set of reaction parameters.

21. The method of claim 17, further comprising diluting the sample, conditioning the sample, or both diluting and conditioning the sample prior to flowing the sample through the at least two detectors.

22. The method of claim 17, further comprising subjecting the sample to a chromatographic separator after the detecting step.

23. The method of claim 17, further comprising flowing the sample through at least three detectors.

24. The method of claim 23, wherein each detector is the same type of detector, and each detector detects the same property of the polymer at a different condition.

25. The method of claim 23, wherein at least one detector detects a different property of the polymer.

26. The method of claim 17, wherein the property of the polymer that each of the at least two detectors detect is selected from the group consisting of light scattering, ultraviolet/visible absorption, refractometry, viscometry, conductivity, pH, polarimetry, turbidity, fluorescence, circular dichroism, and birefringement.

27. The method of claim 17, wherein each condition is selected from the group consisting of temperature, ionic strength, pH, solution composition, and radiation.

28. The method of claim 27, wherein the solution composition comprises one or more of a salt, a dye, a small molecule, a pigment, a nanoparticle, a surfactant, and a second polymer.

29. A method of controlling a property of a polymer, the method comprising
(a) synthesizing a polymer in a reactor under a first set of reaction parameters;
(b) extracting a sample of the polymer from the reactor during the synthesis;
(c) flowing the sample through at least two detectors;
(d) detecting a property of the polymer at each of the at least two detectors to produce at least two signals, each detector being the same type of detector, and each detector detecting the same polymer property at a different condition;
(e) analyzing the at least two signals to determine the polymer property at each condition;
(f) modifying the first set of reaction parameters to a second set of reaction parameters, based on the analysis of the signal from each detector; and
(g) synthesizing the polymer in the reactor under the second set of reaction parameters.

* * * * *